United States Patent
Van Gompel et al.

(10) Patent No.: US 7,635,360 B2
(45) Date of Patent: *Dec. 22, 2009

(54) METHOD FOR THE MANUFACTURE OF A DISPOSABLE UNDERGARMENT HAVING A CUTOUT

(75) Inventors: Paul T. Van Gompel, Hortonville, WI (US); Russell E. Thorson, Appleton, WI (US); Kenneth J. Wagner, Greenville, WI (US); Jean F. Niemeyer, Appleton, WI (US); Judith A. Musil, Appleton, WI (US); Heidi K. Wudi, Appleton, WI (US); Bridget A. Balogh, Menasha, WI (US); Cindi Maas, Appleton, WI (US); Steve Veith, Menasha, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 627 days.

This patent is subject to a terminal disclaimer.

(21) Appl. No.: 10/624,660

(22) Filed: Jul. 22, 2003

(65) Prior Publication Data

US 2005/0020992 A1    Jan. 27, 2005

(51) Int. Cl.
*A61F 13/495*    (2006.01)
*B32B 38/10*    (2006.01)
(52) U.S. Cl. .................. 604/385.19; 156/164; 156/267
(58) Field of Classification Search ............ 604/385.19, 604/398, 392, 393, 395, 402
See application file for complete search history.

(56) References Cited

U.S. PATENT DOCUMENTS

| | | | |
|---|---|---|---|
| 3,488,778 A * | 1/1970 | Goujon et al. ................ | 2/402 |
| 3,895,629 A | 7/1975 | Snyder | |
| 4,036,233 A | 7/1977 | Kozak | |
| 4,326,302 A * | 4/1982 | Lowe et al. .................... | 2/405 |
| 4,406,723 A * | 9/1983 | Marra et al. ................... | 156/98 |
| 4,612,674 A * | 9/1986 | Hashimoto .................... | 2/406 |
| 4,662,874 A | 5/1987 | Korpman | |

(Continued)

FOREIGN PATENT DOCUMENTS

EP    0 648 482 A2    4/1995

(Continued)

OTHER PUBLICATIONS

U.S. Appl. No. 09/855,182, filed May 15, 2001 for "Absorbent Garment with Expandable Absorbent Element," Fell et al.

(Continued)

*Primary Examiner*—Tatyana Zalukaeva
*Assistant Examiner*—Paula L Craig
(74) *Attorney, Agent, or Firm*—H. Michael Kubicki

(57) ABSTRACT

A method of manufacturing an undergarment includes moving a web of body panel material in a longitudinal machine direction, forming a cutout in the web, cutting the web of body panel material along the longitudinal machine direction and thereby forming a rear body panel web and a front body panel web, and connecting a crotch member to each of the rear and front body panel webs. The crotch member covers said cutout when connected to the rear and front body panel webs. A disposable undergarment having a cutout, and a method for the use thereof, is also provided.

17 Claims, 10 Drawing Sheets

U.S. PATENT DOCUMENTS

| | | | |
|---|---|---|---|
| 4,753,646 A * | 6/1988 | Enloe | 604/385.29 |
| 4,760,764 A * | 8/1988 | De Jonckheere et al. | 83/23 |
| 4,834,737 A | 5/1989 | Khan | |
| 4,920,840 A * | 5/1990 | Fink | 83/140 |
| 4,941,933 A | 7/1990 | Korpman | |
| 4,965,122 A * | 10/1990 | Morman | 442/328 |
| 5,037,413 A * | 8/1991 | Haque | 604/385.19 |
| 5,062,840 A | 11/1991 | Holt et al. | |
| 5,110,386 A * | 5/1992 | Ochi et al. | 156/204 |
| 5,226,992 A * | 7/1993 | Morman | 156/62.4 |
| 5,383,867 A * | 1/1995 | Klinger | 604/385.23 |
| 5,451,442 A * | 9/1995 | Pieniak et al. | 428/54 |
| 5,554,149 A * | 9/1996 | O'Donnell | 604/385.19 |
| 5,555,847 A * | 9/1996 | Kelly | 119/850 |
| 5,569,229 A * | 10/1996 | Rogers | 604/385.09 |
| 5,624,422 A | 4/1997 | Allen | |
| 5,705,013 A * | 1/1998 | Nease et al. | 156/260 |
| 5,725,714 A * | 3/1998 | Fujioka et al. | 156/259 |
| 5,804,021 A | 9/1998 | Abuto et al. | |
| 5,843,065 A * | 12/1998 | Wyant | 604/385.09 |
| 5,858,151 A | 1/1999 | Igaue et al. | |
| 5,873,868 A | 2/1999 | Nakahata | |
| 6,217,563 B1 | 4/2001 | Van Gompel et al. | |
| 6,222,092 B1 | 4/2001 | Hansen et al. | |
| 6,264,641 B1 | 7/2001 | Van Gompel et al. | |
| 6,395,955 B1 * | 5/2002 | Roe et al. | 604/361 |
| 6,472,045 B1 * | 10/2002 | Morman et al. | 428/131 |
| 6,527,756 B1 * | 3/2003 | Mishima et al. | 604/385.19 |
| 6,570,056 B1 * | 5/2003 | Tanzer et al. | 604/368 |
| 6,635,135 B2 * | 10/2003 | Kuen et al. | 156/199 |
| 6,682,626 B2 * | 1/2004 | Mlinar et al. | 156/252 |
| 6,827,804 B2 * | 12/2004 | Otsubo et al. | 156/161 |
| 6,911,106 B2 | 6/2005 | Otsubo et al. | |
| 6,979,380 B2 * | 12/2005 | Thorson et al. | 156/259 |
| 7,014,632 B2 * | 3/2006 | Takino et al. | 604/393 |
| 7,220,335 B2 * | 5/2007 | Van Gompel et al. | 156/259 |
| 7,314,465 B2 * | 1/2008 | Van Gompel et al. | 604/395 |
| 7,419,562 B2 * | 9/2008 | Van Gompel et al. | 156/259 |
| 2002/0148557 A1 * | 10/2002 | Heller et al. | 156/252 |
| 2002/0151860 A1 * | 10/2002 | Klemp et al. | 604/385.19 |
| 2002/0151864 A1 | 10/2002 | Otsubo et al. | |
| 2002/0169432 A1 * | 11/2002 | Fell et al. | 604/385.14 |
| 2003/0051802 A1 * | 3/2003 | Hargett et al. | 156/256 |
| 2003/0054930 A1 * | 3/2003 | Conger | 493/373 |
| 2003/0132549 A1 * | 7/2003 | Mlinar et al. | 264/293 |
| 2003/0168159 A1 * | 9/2003 | Een et al. | 156/264 |
| 2003/0230378 A1 * | 12/2003 | Olsson et al. | 156/164 |
| 2004/0060648 A1 * | 4/2004 | Thorson et al. | 156/258 |
| 2004/0064121 A1 * | 4/2004 | Van Gompel et al. | 604/385.01 |
| 2004/0068246 A1 * | 4/2004 | Rose et al. | 604/385.27 |
| 2004/0108054 A1 * | 6/2004 | Otsubo et al. | 156/259 |
| 2004/0122397 A1 * | 6/2004 | Morman et al. | 604/385.01 |
| 2004/0210206 A1 * | 10/2004 | Coates | 604/386 |
| 2005/0010188 A1 * | 1/2005 | Glaug et al. | 604/396 |

FOREIGN PATENT DOCUMENTS

| | | |
|---|---|---|
| EP | 1 240 881 A2 | 9/2002 |
| EP | 1 350 498 A1 | 10/2003 |
| FR | 1 177 805 A | 4/1959 |
| GB | 2 218 322 A | 11/1989 |
| JP | 03176053 A | 7/1981 |
| JP | 60-194947 | 10/1985 |
| WO | WO 2005/007051 A1 | 1/2005 |

OTHER PUBLICATIONS

U.S. Appl. No. 10/624,333, filed Jul. 22, 2003 for "Disposable Undergarment Having a Slit and Method for the Manufacture Thereof," Van Gompel et al.

International Search Report in International Application No. PCT/US04/010159, dated Oct. 4, 2004, 4 pages.

* cited by examiner

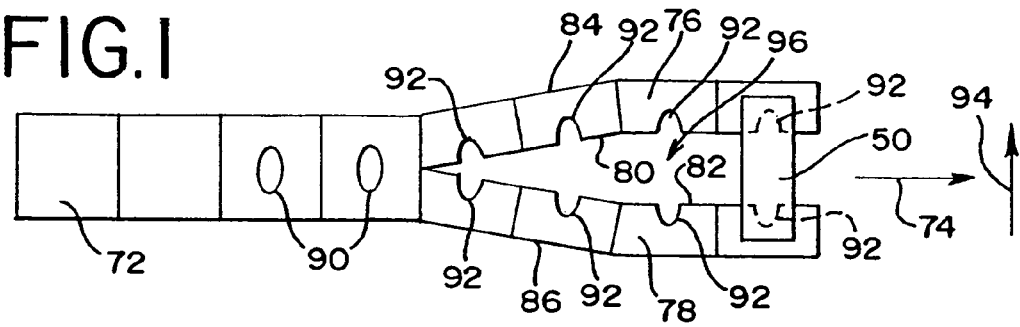
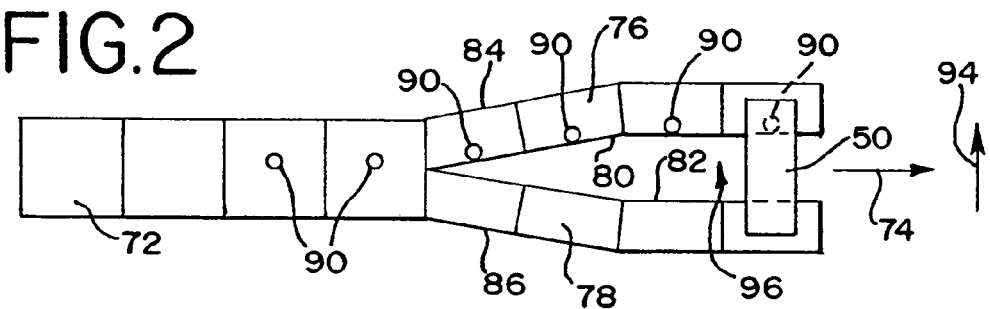
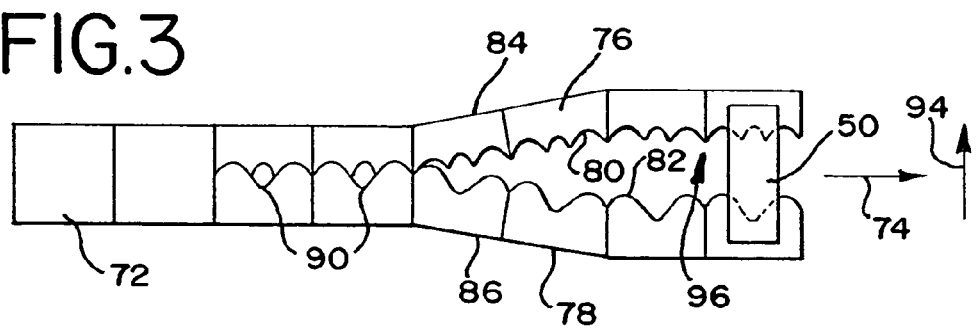
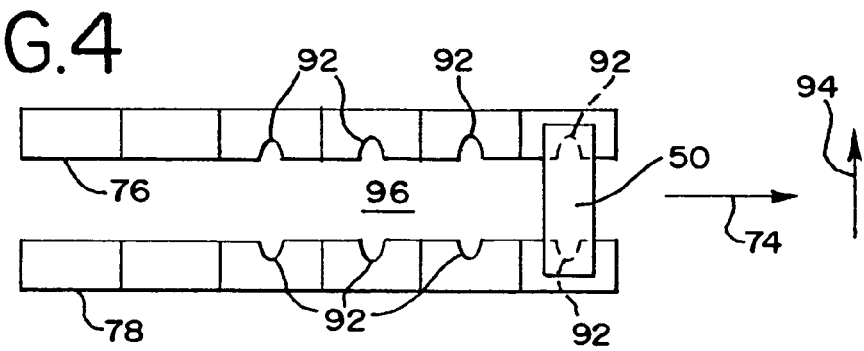
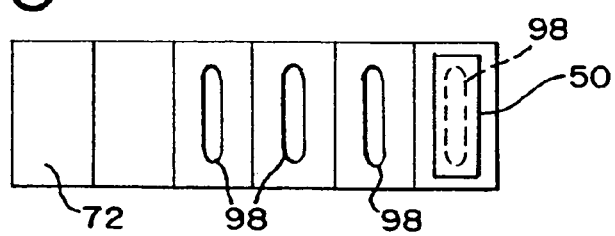

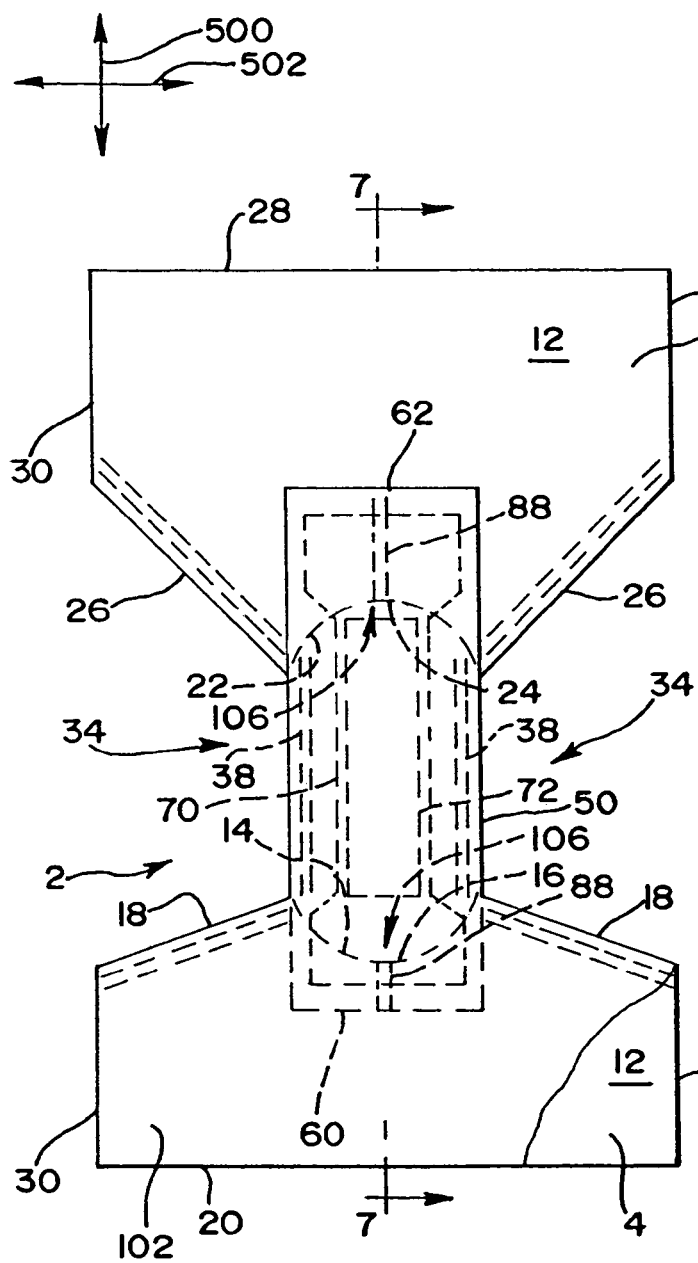
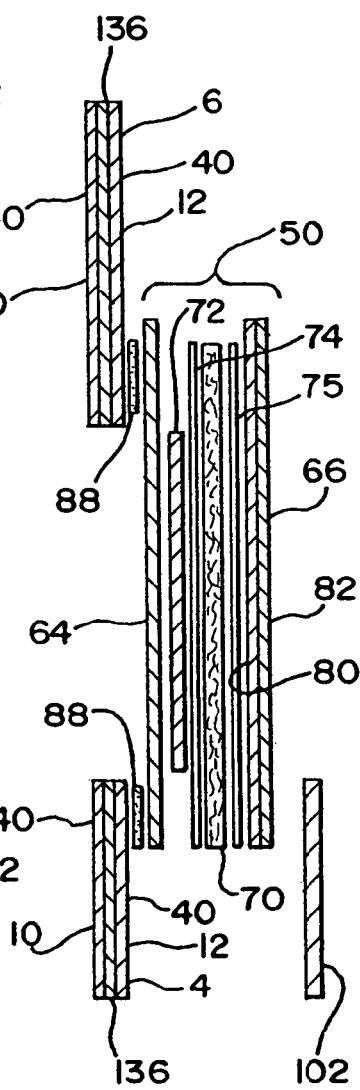

METHOD FOR THE MANUFACTURE OF A DISPOSABLE UNDERGARMENT HAVING A CUTOUT

BACKGROUND

The present invention relates generally to disposable undergarments, and in particular, to an undergarment including one or more components with a discontinuity, such as a slit or cutout, and to the method for the manufacture thereof.

Disposable undergarments can be configured in many different forms. For example, disposable absorbent garments can be configured as a pant-type, pull-on garment, or as a diaper-type product that is drawn up between the legs and fastened about the waist with various fastening systems. Typically, the undergarment includes a body chassis, which is secured to the body of the user. In some embodiments, the disposable garment includes a front and rear body panel connected to an absorbent insert. Often, the absorbent insert is secured to a bodyside surface of the body panels, or is sandwiched between a body panel and an outer cover, which body panels and/or outer cover restrict the ability of the absorbent insert to expand away from the body of the user.

Often, one or more components of the body chassis, such as the outer cover, are made from a single piece of material, with leg openings cut therein, for example by die cutting. The material from the leg cut out, which can account for as much as 20-30% of the total area of the outer cover, typically is waste material, which must be disposed of or recycled. In addition, the size of the leg openings formed by a die cutter in a conventional one-piece outer cover is typically fixed. As such, it can be expensive and time consuming, and reduces the overall flexibility of the manufacturing line, to switch dies and alter the process to manufacture different size garments.

In response to this problem of waste, some garments are configured with front and rear sections formed from a single web that is divided into two nested halves, as disclosed for example in U.S. Pat. No. 5,858,151 and Japanese Patent Application 03-176053 A. However, the webs of the U.S. Pat. No. 5,858,151 have overlapping crotch portions that are directly secured one to the other. Accordingly, the overall rise of the garment is not readily varied to accommodate different size users, and the range of sizes is limited by the extent of the overlapping regions.

The diaper body of Japanese Patent Application 03-176053 A requires the two webs to be shifted in the machine direction, with a diaper body then positioned over opposed recesses formed in the front and back waistband. The diaper body, however, is secured to the body side surface of the waistbands. As such, the waistbands can restrict the ability of diaper body to expand away from the body of the user.

In addition, some disposable undergarments are made of one or more elastic materials laminated to a non-elastic material. In some garments, slits are provided in one of the layers, e.g., the non-elastic material, to allow the laminate to expand, but the slit does not provide a discontinuity through the entire laminate or the layer of elastic material. In other undergarments, an elastic material, such as a top sheet that extends the length of the garment, is provided with slits that open to permit the passage of exudates therethrough.

SUMMARY

Briefly stated, in one aspect, a method of manufacturing an undergarment includes moving a web of body panel material in a longitudinal machine direction, forming a cutout in the web, cutting the web of body panel material along the longitudinal machine direction and thereby forming a rear body panel web and a front body panel web, and connecting a crotch member to each of the rear and front body panel webs. The crotch member covers the cutout when connected to the rear and front body panel webs.

In another aspect, a method of manufacturing a disposable undergarment includes moving a web of body panel material in a longitudinal machine direction, forming a cross-machine direction slit in the web, and connecting a crotch member to the web. The crotch member extends in the cross-machine direction and covers the slit.

In another aspect, a disposable undergarment includes a body chassis having at least one unitary web with first and second terminal edges defining front and rear waist edges respectively. The web has an opening formed in a crotch region thereof, wherein the body chassis has a garment side surface and a body side surface. An absorbent insert is secured to the body side surface of the body chassis and covers the opening in the web. At least a portion of the absorbent insert is adapted to extend through the opening in the web when the absorbent insert is insulted with bodily exudates.

In yet another aspect, a disposable undergarment includes a front body panel having a body side surface and a garment side surface, a pair of opposite first laterally spaced side edges, a first waist edge and a first crotch edge longitudinally spaced from the first waist edge. The undergarment further includes a rear body panel having a body side surface and a garment side surface, a pair of opposite laterally spaced second side edges, a second waist edge and a second crotch edge longitudinally spaced from the second waist edge. The first and second crotch edges are longitudinally spaced from each other. At least one of the front and rear body panels has a cutout formed therein adjacent respectively at least one of the first and second crotch edges. A crotch member is connected to the garment side surfaces of the front and rear body panels and covers the cutout. An outer cover has a length less than a length of the undergarment measured between the respective first and second waist edges. The outer cover is secured to the garment side surface of the at least one front and rear body panel having the cutout and covers a portion of the crotch member connected thereto.

In yet another aspect, a disposable undergarment includes a front body panel having a pair of opposite first laterally spaced side edges, a first waist edge and a first crotch edge longitudinally spaced from the first waist edge. A rear body panel has a pair of opposite laterally spaced second side edges, a second waist edge and a second crotch edge longitudinally spaced from the second waist edge. The first and second crotch edges are longitudinally spaced from each other, and at least one of the first and second crotch edges has at least one longitudinally extending slit formed therein. A crotch member is connected to the front and rear body panels and covers the at least one slit.

The various aspects provide significant advantages over other disposable undergarments and methods. For example and without limitation, the cutout formed in the front and rear body panels provides access to the crotch member connected to the garment side of the body panels, e.g., to permit passage of exudates to the crotch member. Conversely, if the crotch member is secured to the body side surface of the body panels, the cutout allows the crotch member to expand away from the body of the user, for example when insulted.

The slit formed in one or both of the front and rear body panels also provides significant advantages. In particular, the slit reduces the force required to elongate the body panels as the garment is applied to the user. In addition, the slit, when opened, provides access to a crotch member secured to the garment side surface of a body panel, or allows the crotch member to expand away from the body of the user if secured to the body side surface of the body panel.

The foregoing paragraphs have been provided by way of general introduction, and are not intended to limit the scope of the following claims. The presently preferred embodiments, together with further advantages, will be best understood by reference to the following detailed description taken in conjunction with the accompanying drawings.

BRIEF DESCRIPTION OF THE DRAWINGS

FIG. 1 is a schematic plan view illustration of a method of manufacturing an absorbent garment.

FIG. 2 is a schematic plan view illustration of an alternative method of manufacturing an absorbent garment.

FIG. 3 is a schematic plan view illustration of an alternative method of manufacturing an absorbent garment.

FIG. 4 is a schematic plan view illustration of an alternative method of manufacturing an absorbent garment.

FIG. 5 is a schematic plan view illustration of an alternative method of manufacturing an absorbent garment.

FIG. 6 is a garment side plan view of a disposable undergarment in an open condition, with a partial cut-away section of a front body panel.

FIG. 7 is a cross-sectional view of a disposable undergarment taken along line 7-7 of FIG. 6.

DETAILED DESCRIPTION OF THE PRESENTLY PREFERRED EMBODIMENTS

Figure 10:
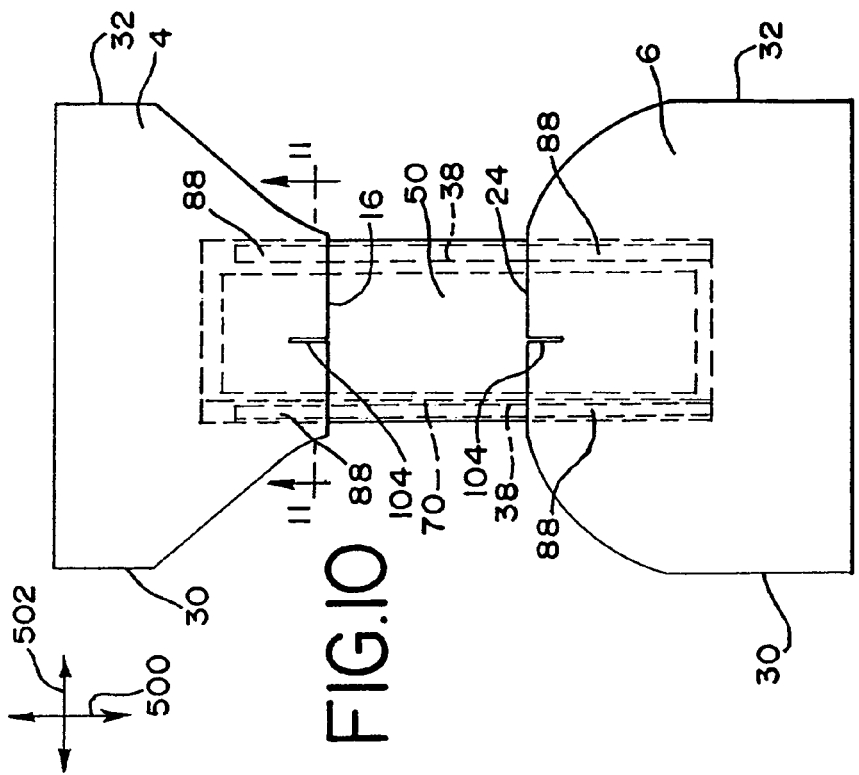
FIG. 10 is a garment side plan view of an alternative embodiment of a disposable undergarment in an open condition.
Figure 11:
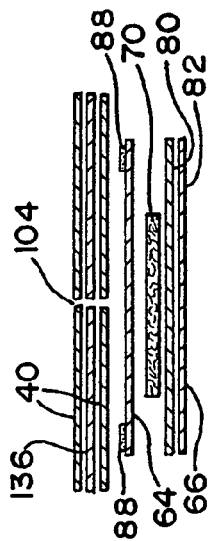
FIG. 11 is a cross-sectional view of a disposable undergarment taken along line 11-11 of FIG. 10.
Figure 8:
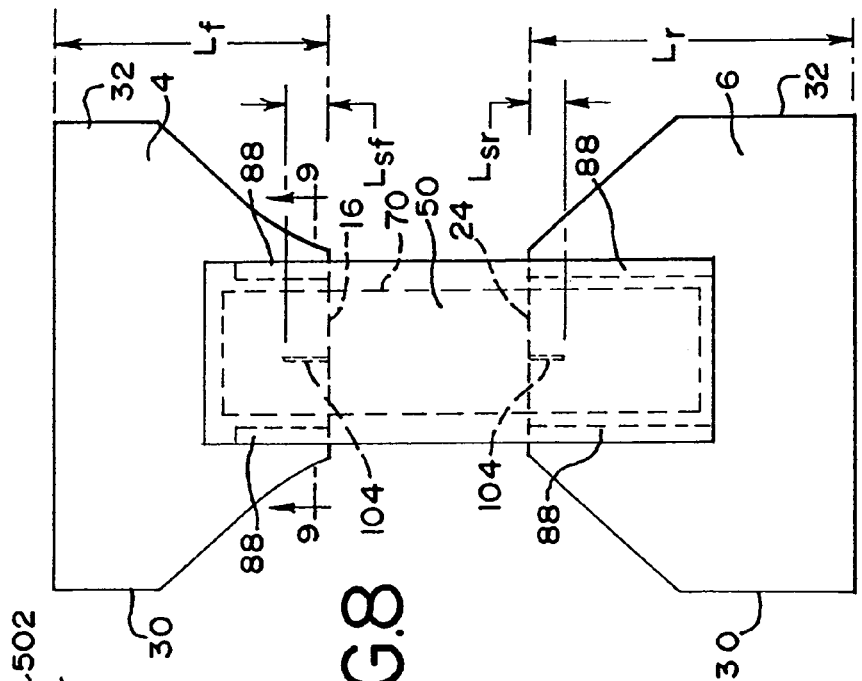
FIG. 8 is a body side plan view of an alternative embodiment of a disposable undergarment in an open condition.
Figure 9:
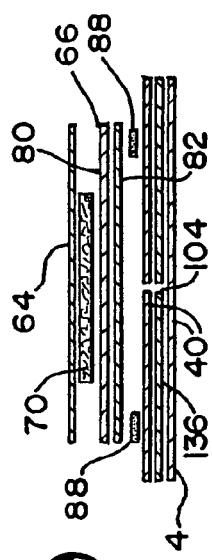
FIG. 9 is a cross-sectional view of a disposable undergarment taken along line 9-9 of FIG. 8.

It should be understood that the term "longitudinal," as used herein, means of or relating to length or the lengthwise direction 500. The term "laterally," as used herein, means situated on, directed toward or running from side to side. The term "first direction" generally refers to a path, line or course rather than a vector, and includes and applies equally to opposite orientations along the path, line or course, including for example and without limitation movement along a path, line or course in both directions (as indicated by the bi-directional arrows associated with the longitudinal and lateral directions 500, 502 in FIGS. 6, 8 and 10). Likewise, the term "second direction" generally refers to a path, line or course rather than a vector (not orientation dependent), and includes for example and without limitation movement along a path, line or course in both directions. In one example, the first direction is defined by and refers to one of the longitudinal and lateral directions, while the second direction refers to the other of the longitudinal and lateral directions.

The term "bodyside" should not be interpreted to mean in contact with the body of the user, but rather simply means the side that would face toward the body of the user, regardless of whether an undergarment is actually being worn by the user and regardless of whether there are or may be intervening layers between the component and the body of the user. Likewise, the term "garment side" should not be interpreted to mean in contact with the garments of the user, but rather simply means the side that faces away from the body of the user, and therefore toward any outer garments that may be worn by the user, regardless of whether the undergarment is actually being worn by a user, regardless of whether any such outer garments are actually worn and regardless of whether there may be intervening layers between the component and any outer garment.

The term "machine direction" means the direction of flow as the various members and webs progress along the fabrication line and process. It should be understood that various separate members or webs can each be traveling in a machine direction, but with the various machine directions not necessarily being parallel or oriented in the same direction. For example, a first component such as a web may be traveling a first machine direction, which is substantially perpendicular to the travel of another component, such as an absorbent insert, in a second machine direction.

The term "cross-machine direction" or "cross direction" means the direction substantially perpendicular to the machine direction.

The term "downstream" means that one item is positioned more closely to the output or finished product end of the machine and/or process relative to another item. Conversely, the term "upstream" means that an item is positioned more closely to the input end of the machine or process relative to another item. For example, the output end is downstream of the input end, and vice versa, the input end is upstream of the output end.

The phrases "removeably attached," "removeably attaching," "removeably connected," "removeably engaged," "releasably attached," "releasably connected," or "releasably engaged," and variations thereof, refers to two or more elements being connected or connectable such that the elements tend to remain connected absent a separation force applied to one, both or all of the elements, and where the elements are capable of being separated upon the application of a separation force. The required separation force is typically beyond that encountered while wearing the absorbent garment.

The phrases "fixedly secured," "fixedly engaged," "fixedly attached," "fixedly connected," and variations thereof, refers to two or more elements being connected or connectable such that they are not disconnected or otherwise separated, and are not intended to be separated or disconnected, during the normal operation and use of the absorbent garment.

The term "web" refers to a continuous stream of material, whether made from one or more layers or substrates, and regardless of whether it may have non-continuous, discrete items disposed thereon.

The terms "connecting," "coupled," "attached," and "secured," and variations thereof, broadly covers two or more items being directly connected one to the other, or by way of one or more intervening members or components.

The term "cutout" means that a portion of material is removed. The term "slit" refers to a cut wherein no material is removed.

Referring to FIGS. 6-11, an undergarment 2 includes a first, front body panel 4 and a second, rear body panel 6. The term "body panel" refers to the portion(s) of the undergarment, whether made of one or more layers or substrates or of one or more pieces or components, that is/are fitted circumferentially around at least the waist region of the user, including for example the user's lower back, buttock, hips and abdomen. The first and second body panels each have an inner, bodyside surface 10 and an outer, garment side surface 12. The first, front body panel 4 has a first edge 14 forming a crotch portion 16 and leg opening portion 18 and a second terminal edge 20 that, in one embodiment, is linear but can assume other shapes. Likewise, the second, rear body panel 6 has a first edge 22 forming a crotch portion 24 and a leg opening portion 26 and a second terminal edge 28, which is shown linear but can assume other shapes. Each of the first and second body panels has an outboard side edge 30, 32 formed along the outer periphery of the opposite side portions of the first and second body panel. It should be understood that the outboard side edges of the front and rear body panels could have the same or different lengths relative to each other.

One or more, and in one embodiment a plurality, meaning two or more, elastic elements are secured to each of the first and second body panels. In one embodiment, a plurality of elastic elements are spaced across substantially the entire waist portion of the front and rear body panel although they may be spaced across a lesser length. For example, elastic elements can extend along the upper waist portion and along the lower terminal edge defining in part a leg opening 34. The elastic elements can extend along the entirety of the edges 14, 22, or along only the leg opening portions 18, 26 thereof.

In one embodiment, the front body panel has a "non-elasticized" area wherein there are no elastic elements, or other elastic or elastomeric backing members, incorporated therein or making up any portion of the thickness or cross-section of the body panel at that area. It should be understood, that in an alternative embodiment, one or more separate waist bands, with or without elastic elements, can be secured to one or both of the rear and front body panels, preferably along the upper terminal edges 20, 28 thereof. Likewise, one or more separate leg bands can be secured to one or both of the rear and front body panels along the leg open portions 18, 26 adjacent the leg openings 34. Alternatively, one or both of the body panels can be formed without any elastic elements.

The various waist and leg elastic elements can be formed from rubber or other elastomeric materials. One suitable material is a LYCRA® elastic material. For example, the various elastic elements can be formed of LYCRA® XA Spandex 540, 740 or 940 decitex T-127 or T-128 elastics available from E.I. duPont De Nemours and Company, having an office in Wilmington, Del.

Each body panel 4, 6 is preferably formed as a composite, or laminate material, otherwise referred to as substrates or laminates, with an elastic core 136 sandwiched therebetween. In one embodiment, the elastic core 136 is made of an elastomeric film or nonwoven elastic or stretchable material including for example but not limited to styrenic copolymers of polyisoprene, polybutadiene or polyolefin, copolymers of polyolefins, natural or styrene butadiene rubber, polyurethanes, polyamides, polyesters, and co-extrusions/blends of the aforementioned materials. The elastic core can be formed as a membrane or from a plurality of elastic strands, as described above. In one embodiment, two or more layers 40 are bonded to the elastic core 136, and/or each other, with various adhesives, such as hot melt, or by other techniques, including for example and without limitation ultrasonic bonding and heat pressure sealing. In one embodiment, the two layers are made of a non-woven material such as a spunbond material, a bonded carded material or other known materials. In this way, the body panels are made of a stretchable/elastic material.

As used herein, the interchangeable terms "stretchable" and "elastic," and variations thereof, refer to a material that can elongate or deform (stretch) in response to the application of a tensile force, and upon removal of the tensile force the material can retract and become shorter. Because of hysteresis, the material may not be able to fully recover or return to its original, pre-stretched length. Thus, a stretchable or elastic material can be stretched and upon relaxing the material, will tend to resume its original shape.

As used herein, the term "extensible" means capable of being extended, and that it provides a selected elongation when subjected to an applied tensile force, while also providing a selected, sustained deformation when subjected to an applied tensile force and then allowed to relax for a selected time period beginning immediately after removal of the tensile force. Preferably the sustained deformation is substantially permanent deformation. The selected elongation and sustained deformation preferably occur at least along the lateral cross-direction of the garment, although it should be understood that it also could occur along the longitudinal direction, or both. In one embodiment, the material is capable of providing an elongation of at least about 1 cm when subjected to a tensile force of 11.8 g/cm, and further provides a substantially permanent deformation of at least about 20% when subjected to a tensile force of 19.70 g/cm and is then allowed to relax under a zero applied stress for a period of 1 minute. Various extensible materials, and other acceptable materials that can be used for the body panels and the absorbent composite, which may include without limitations a retention portion, a topsheet and a backsheet, are described in U.S. Pat. No. 6,264,641, entitled Expandable Cover Garment, the entire disclosure of which is hereby incorporated herein by reference.

A suitable technique for generating a representative tensile-load vs. extension curve, and for determining the amount of elongation and/or retractive force parameters of a selected component or material can employ ASTM Standard Test Method D882 (Tensile Method for Tensile Properties of Thin Plastic Sheeting) dated December 1995, with the following particulars. The "width" of the test sample will be a cross-wise width which can be conveniently obtained from the product being tested, and is desirably about 2 inch (about 5.04 cm). The test sample width is perpendicular to the direction of the tensile force applied during the testing. With regard to the shown configurations, for example, the test sample "width" generally corresponds to the length-wise dimension of the component along the longitudinal direction of the article. The initial separation of the jaws of the tensile tester is 3 inches (7.62 cm), and the moving jaw is moved at a constant rate of 50 mm/min. The moving jaw is stopped at an extension of 50 mm for a period of 10 sec, and then returned back to its initial starting position at a rate of 50 mm/min. The force-extention curve to the complete tension and retraction cycle can be recorded on a conventional computer equipped with commercially available software, such as TestWorks for Windows, version 3.09, which is available from MTS System Corporation, a business having a location at 14000 Technology Drive, Eden Prairie, Minn. The obtained data is normalized and reported in appropriate units of force per unit length of sample "width" (e.g. grams-force per inch, or Newtons per inch, or grams-force per centimeter, or Newtons per centimeter).

It should be understood that the body panels can be made of a single layer or substrate of non-woven material, a bi-layer substrate made of non-woven materials without an elastic core, or more than two layers or substrates. Of course, it should be understood that other knitted or woven fabrics, non-woven fabrics, elastomeric materials, polymer films, laminates and the like can be used to form one or more of the body panel layers. The term "non-woven" web or material, as used herein, means a web having a structure of individual fibers or filaments that are interlaid, but not in an identifiable manner and without the aid of textile weaving or knitting, as in a knitted or woven fabric.

In one embodiment, the body panel material can be secured to the elastic core, such as an elastomeric layer or elastic strands or ribbons, which have been elongated and retracted, such that the material is gathered when the elastic element(s) are relaxed. Alternatively, the material can be gathered and laminated to non-elongated elastic elements. In one preferred embodiment, the body panel includes a gathered elastic laminate made from nonwoven base sheets bonded with elongated elastic elements sandwiched therebetween.

In various preferred embodiments, the body panel material may be substantially permeable to air or substantially impermeable to air. The body panel material also may be substantially liquid-permeable or substantially liquid-impermeable. In particular arrangements, the body panel material may be substantially nonelastomeric. In other aspects, the body panels can include an elastomeric material that is elastomerically stretchable at least along one or both of the lateral article width and the longitudinal article length. Examples of such elastomeric composite materials can include a continuous filament stretch bonded laminate (CFSBL), a vertical filament laminate (VFL), neck-bonded-laminate (NBL), a stretch-bonded-laminate (SBL), a necked-stretch bonded laminate (NSBL) or a necked-thermal laminate, or the like, as well as combinations thereof. Exemplary CFSBL, NBL, SBL, and NSBL materials are described in U.S. Pat. Nos. 5,226,992, 4,981,747, 4,965,122, 5,336,545, 5,385,775, 5,414,470, 4,720,415, 4,789,699, 4,781,966, 4,657,802, 4,652,487, 4,655,760, 5,116,662 and 5,114,781, and 6,323,389, all of which are hereby incorporated herein by reference. Exemplary VFL materials are described in U.S. Provisional Patent Application Ser. No. 60/204,307, filed May 15, 2000 and entitled "Method and Apparatus for Producing Laminated Articles," and PCT application WO 01/88245 A2, both assigned to Kimberly-Clark Worldwide, Inc., the Assignee of the present application, with the entire disclosures of both being hereby incorporated herein by reference. Such laminates can provide an improved combination of cloth-like feel and elastomeric stretchability. The body panels can be composed of materials that are elastic or elastomeric and exhibit biaxial stretch characteristics or lateral/longitudinal stretch characteristics, or which are extensible composites. Additional waist and leg elastic elements can be added to, but are not necessarily required by, the body panels.

In one embodiment, the body panel material is extensible but not elasticized. For example, the body panel can be made of a film or non-woven that is attached, by way of adhesives or thermal bonding, to an extensible non-woven material. Alternatively, the body panel can be made of a low modulus film such as ethylene methyl acrylate (EMA).

As shown in the embodiments of FIGS. 6-11, the entirety of the body panels 4, 6 are elasticized, such that the entirety of each of the body panels can elongate and conform to the body of the user without any substantial spacing between the body panel and the user's body, and without the attendant bulkiness of a non-elasticized material.

In one embodiment, the body panels are breathable, cloth-like, multi-directional nonwoven laminates with stretch or extensible properties. In one embodiment, the non-woven layers are pre-necked, for example between about 10% and about 80%, in the longitudinal direction, which provides extensibility in the longitudinal direction with minimal force.

In one embodiment, the body panel members 4, 6 are made of non-woven laminates of two layers of longitudinally extensible 0.60 osy polypropylene spunbond material with elongated strands of Lycra® elastic sandwiched between the spunbond layers and thereafter adhesively bonded. In particular, the body panel material is necked in the cross direction. As used herein, the term "necked," and variations thereof, refers to any material that has been constricted in at least one dimension by applying a tensioning force in a direction that is perpendicular to the desired direction of neck-down. Processes that may be used to constrict a material in such a manner include, for example and without limitation, drawing processes. The elastics are then elongated in the machine direction and secured to the body panel material. The elastics are then allowed to retract so as to gather the necked spunbond material in the lateral (machine) direction thereby creating an elastically gathered non-woven body panel with longitudinal extensibility. The term "gather," and variations thereof, as used herein means puckered, or contracted into folds or wrinkles, which should be understood as including micro-pleats.

In this way, the body panel can be elongated in both the longitudinal and lateral direction to conform to the body of the user when the garment is applied thereto. In particular, as the user pulls the garment up over their hips, the non-woven laminate body panels stretch in the lateral direction while the leg regions of the front and rear body panels conform to the crotch and bodylines of the user. At the same time, the body panel material extends in the longitudinal direction to conform to the buttocks and stomach of the user. The extensibility of the body panels follows the natural curvature of user's body to provide conformance thereto. As the body panel extends in the longitudinal direction, the spacing between the laterally extending elastic elements, incorporated in one embodiment, will increase.

The body panel non-woven material is preferably substantially hydrophobic, which may optionally be treated with a surfactant or otherwise processed to impart a desired level of wettability and hydrophilicity. In one particular embodiment of the invention, the body panel is a nonwoven, wire-weave spunbond polypropylene fabric composed of about 1.6 denier fibers formed into a web having a basis weight of about 0.6 osy. One suitable non-woven material is the Corinth 0.60 osy, 1.6 dpf wireweave, nonwettable Metallocene (EXXON ACHIEVE 2854 PP) spunbond material manufactured by Kimberly-Clark Corporation, the assignee of the present application.

The crotch member 50 of the various undergarments connecting the front and rear body panels 4, 6 can be folded such that the side edges 30, 32 of the front and rear body panels 4, 6 are aligned, whereinafter they can be fixedly secured at a seam to form the leg opening 34. The seam can be formed by bonding, sewing or otherwise attaching the side edges. Alternatively, the product can remain "open," wherein the body panels are releasably secured with one or more fastening members as explained below.

In one embodiment, the garment includes a combination of side edges that are secured to form a seam and fastening members that allow the fit of the undergarment to be adjusted. In other embodiments, the fastening elements are used alone without a seam. For example, in one embodiment, fastening members are preferably attached to the front body panel and extend inboard relative to the outboard side edge of the front body panel from an attachment location, which is preferably spaced inboard from the side edge. A landing member can be formed on or secured to the body panel to receive a refastenable portion of the fastening member. One or more lines of weakness can be provided along the front or rear body panel such that one or both of the body panels are breakable. The lines of weakness can comprise a perforation or other series of cuts, a thinning, breakage or separation of material, or a strip of a different kind of material bridging portions of the body panel that is more easily torn or broken than the other material thereof, which allow a user or the manufacturer to separate portions of the body panel. For example, the undergarment can be broken along the lines of weakness after the garment is applied to a user, or beforehand. In one embodiment, the fastening members are secured to the garment-side surface of the body panel.

It should be understood that, in other embodiments, the fastening members can be secured to the rear body panel and engage the front body panel or, conversely, can be secured to the front body panel and engage the rear body panel, preferably along at least a portion that is not elasticized. In one embodiment, the fastening members are fixedly secured to the outer, garment-side surface of the front and/or rear body panels, and releasably engage the outer, garment-side surface of the front and/or rear body panels, although it should be understood that the fastening members could be fixedly secured to an inner body-side surface of front and/or rear body panels and releasably engage an inner, body-side surface of the front and/or rear body panels.

When incorporated into a disposable absorbent undergarment, the fastening members can include a refastenable portion, such as an array of hook members, adhesives, such as pressure sensitive adhesives, buttons, zippers, snaps and other releasable and reattachable fastening devices. In various embodiments, the fastening member includes one, two or more than two tab members. In one embodiment, the fastening members comprise a carrier member, which is preferably fixedly secured to the side portions of the front body panel with adhesive bonds, sonic bonds, thermal bonds, pinning, stitching or other known types of attachment. In alternative embodiments, the fastening members can be fixedly secured to the rear body panel or to one or both of the front and rear body panels, for example, at the seam, as explained above.

Referring to the embodiments of FIGS. 6-11, the crotch member 50 is formed as a separate subassembly connected to either the bodyside or garment side surface 10, 12 of the body panel members 4, 6. In either embodiment, the crotch member 50 has first and second opposed terminal end edges 60, 62. The crotch member 50 bridges the gap between the terminal edges 14, 22 of the body panels 4, 6 and is connected respectively to those body panels at attachment locations 88. The crotch member 50 that overlaps the body panels or body chassis member can be minimally attached thereto with an attachment having a width of between about 10% and about 100% of the width of the absorbent insert. For example, the crotch member 50 can be attached to the body panels 4, 6 along the longitudinal side edges of the crotch member (FIGS. 8-11), or alternatively along a centerline (FIGS. 6 and 7) such that the edges of the absorbent insert are not attached to the body panels or body chassis. In another embodiment, the entirety of the portion of the crotch member that overlaps the body panels can be attached thereto. The crotch member can be secured to the body panels when they are in a stretched or unstretched condition.

The attachment location can extend along the entire length of the overlapping portion of the crotch member, along only a portion of the length, or at a discrete point, for example proximate midway between the ends 60, 62 of the crotch member. In another embodiment (not shown), the attachment location can be formed from a plurality of discrete attachment locations spaced longitudinally along the centerline. In other alternatives, the terminal edges of the crotch member 50 can be attached to the body panels, or the crotch member can be secured to the body panels along the terminal crotch edges 14, 22 thereof.

In one embodiment, shown in FIGS. 6-11, the crotch member is configured as an absorbent insert 50, which includes a substantially liquid permeable top sheet 64, or liner, and a substantially liquid impermeable back sheet 66. A retention portion 70 is disposed or sandwiched between the topsheet and the backsheet, which are connected. It should be understood that the term "absorbent insert" refers to any material or assembly capable of absorbing liquids or bodily exudates, and may be formed from a single material or component, for example a retention portion, or can be formed as a composite of several components. It should also be understood that the term "crotch member" refers to any member of any material, including for example and without limitation those described herein with respect to the body panels and absorbent inserts, and is no limited to absorbent inserts and/or materials. For example, the crotch member may be made of one or more layers of a non-woven material. It should further be understood that when the crotch member does not include an absorbent material, it could still be used in conjunction with various disposable absorbent pads such as adult incontinent and/or feminine pads so as to improve the performance and comfort of those pads by maintaining them in close proximity to the body of the user.

Referring to FIGS. 6-11, the top sheet 64, back sheet 66 and other components of the absorbent insert can be joined for example with adhesive bonds, sonic bonds, thermal bonds, pinning, stitching or any other attachment techniques known in the art, as well as combinations thereof. For example, a uniform continuous layer of adhesive, a patterned layer of adhesive, a sprayed pattern of adhesive or any array of lines, swirls or spots of construction bonds may be used to join the topsheet and backsheet, or any of the other components described herein.

In one embodiment, one or more crotch elastic members 38 are sandwiched between the top sheet and backsheet along the side edges thereof. The elastic members 38 can extend the entire longitudinal extent of the absorbent insert, or along only a portion thereof.

Additional layers, including for example, a liquid acquisition and distribution layer 72, also referred to as a surge or transfer layer, are also preferably incorporated into the absorbent insert. In one embodiment, the transfer layer does not run the entire length of the absorbent insert and is shorter than the retention portion.

In one embodiment, the retention portion 70, transfer layer 72 and other components, such as tissue layers, are free floating (unattached) between the back sheet 64 and the top sheet 66, which are secured along only the peripheral edges thereof. Alternatively, the retention portion 70, transfer layer 72 and other components are minimally attached to one or both of the back sheet 66 and top sheet 64. For example, the retention portion can be secured to the back sheet along an attachment location positioned along the longitudinal centerline of the retention portion. Alternatively, or in combination with the back sheet connection, the transfer layer or retention portion can be minimally attached to the top sheet. In this way, the retention portion 70, transfer layer 72 and other components do not impede or substantially affect the lateral stretchability and extensibility of the absorbent insert 50 and in particular the top sheet and back sheet, at least one of which is secured to the body chassis.

In another alternative embodiment, the retention portion is secured along the centerline at a point midway between the two ends of the retention portion. In this embodiment, the retention portion also does not restrict or impede the stretchability and extensibility of the absorbent insert, and in particular the top sheet and back sheet, in the lateral or longitudinal directions 500, 502.

In other embodiments, the top sheet is indirectly joined to the backsheet by affixing the topsheet to intermediate layers, such as the surge layer or retention portion, which in turn is affixed to the backsheet. The absorbent insert also may include barrier cuffs, or leakage control shields, formed along the opposite longitudinally extending edges of the absorbent composite.

In one embodiment, the back sheet 66 is a stretchable, elastic, liquid impervious member. Alternatively, the back sheet may be liquid permeable, e.g., when an additional barrier layer is used with the retention portion. In one embodiment, shown in FIG. 7, the back sheet 66 is a laminate structure made of a stretchable, elastic material, such as an elastomeric film 80, which is laminated to an extensible nonwoven material layer 82. It should be understood that the backsheet can be formed from a single layer or substrate or more than two layers or substrates. The backsheet can be stretchable in both the lateral and longitudinal direction, or be stretchable in one direction and extensible in the other.

The backsheet 66 prevents various bodily fluids and exudates from wetting or otherwise contaminating various bedding or outer garments worn by the user over the absorbent garment. The backsheet can be made of the same materials described above in connection with the body panels. In one embodiment, the backsheet can include a film, which can be made of the various materials described above.

The backsheet may include a micro-porous, "breathable" material which permits gases, such as water vapor, to escape from the absorbent garment while substantially preventing liquid exudates from passing through the backsheet. For example, the breathable backsheet may be composed of a microporous polymer film or a nonwoven fabric which has been coated or otherwise modified to impart a desired level of liquid impermeability. For example, a suitable microporous film can be a PMP-1 material, which is available from Mitsui Toatsu Chemicals, Inc., a company having offices in Tokyo, Japan; or an XKO-8044 polyolefin film available from 3M Company of Minneapolis, Minn. The backsheet may also be embossed or otherwise provided with a pattern or matte finish to exhibit a more aesthetically pleasing appearance.

In various embodiments, where a component, such as the backsheet is configured to be permeable to gas while having a resistance and limited permeability to aqueous liquid, the liquid resistant component can have a construction which is capable of supporting a selected hydrohead of water substantially without leakage therethrough. A suitable technique for determining the resistance of a material to liquid penetration is Federal Test Method Standard FTMS 191 Method 5514, 1978, or an equivalent thereof.

In one embodiment, the backsheet is sufficiently impermeable to liquid and semi-liquid materials to substantially prevent the undesired leakage of waste materials, defined as exudates, including for example urine and feces. For example, the backsheet member can desirably support a hydrohead of at least about 45 centimeters (cm) substantially without leakage. The backsheet member can alternatively support a hydrohead of at least about 55 cm, and optionally, can support a hydrohead of at least about 60 cm, or more, to provide improved benefits.

In one example, the backsheet can be composed of a necked fiber, a creped fiber, a micro-pleated fiber, polymer films or the like, as well as combinations thereof. The fabrics may be woven or nonwoven materials, such as spunbond fabrics. One example of a suitable extensible material is a 60% necked, polypropylene spunbond having a basis weight of about 1.2 osy. In one embodiment, the backsheet material is a three-ply laminate having inner and outer facing layers of 0.46 ounces per square yard (osy) polypropylene spunbond material (Kimberly-Clark Delta white polypropylene spunbond) and a middle layer of 10 grams per square meter (gsm) Kraton® 666 elastomer strands (3 mm apart) elongated to 4.5 to 5.5 times. The three piece laminate is adhesively laminated with 2.5 gsm Bostik Findley H2096 adhesive.

In another embodiment, the backsheet is a necked liner laminate made of a two-ply laminate consisting of a soft co-extruded film laminated to a necked nonwoven material. In particular, the material is made of a layer of 0.4 ounces per square yard (osy) polypropylene spunbond material (Kimberly-Clark Delta white polypropylene spunbond) that was necked 35% (to 65% of initial width) to a final basis weight of 0.6 osy and laminated to a Pliant Film XP-8600 0.7 mil (CaCO3 metallocene Dow Affinity and Dowlex 2035 LLDPE co-extruded film).

In another embodiment, the backsheet is a necked liner made of a nonwoven 0.4 ounces per square yard (osy) polypropylene spunbond material (Kimberly-Clark Delta white polypropylene spunbond) that was necked 65% (to 35% of initial width) to a final basis weight of 0.7 osy.

In various constructions, the top sheet 64 can include various woven or nonwoven materials and laminates, which can be stretchable or extensible. In one embodiment, the top sheet 64 is an extensible material, such as a necked spunbond material. For example, the topsheet can be composed of a meltblown or spunbonded web of desired fibers, and may also be a bonded-carded web. For example, the topsheet and liner can be made of a substantially hydrophobic material, and the hydrophobic material may optionally be treated with a surfactant or otherwise processed to import a desired level of wettability and hydrophilicity. In one particular embodiment of the invention, the topsheet is a nonwoven, spunbond polypropylene fabric composed of about 2.8-3.2 denier fibers formed into a web having a basis weight of about 22 gsm and density of about 0.06 gm/cc. The fabric can be surface treated with an operative amount of surfactant, such as about 0.28%

Triton X-102 surfactant. The surfactant can be applied by any conventional means, such as spraying, printing, brush coating or the like. In another embodiment, the top sheet can also include an elastic material, such that it is stretchable.

The retention portion 70 is made of an absorbent material, which can be any material that tends to swell or expand as it absorbs exudates, including various liquids and/or fluids excreted or exuded by the user. For example, the absorbent material can be made of airformed, airlaid and/or wetlaid composites of fibers and high absorbency materials, referred to as superabsorbents. Superabsorbents typically are made of polyacrylic acids, such as FAVOR 880 available from Stockhausen, Inc. of Greensboro, N.C. The fibers can be fluff pulp materials, such as Alliance CR-1654, or any combination of crosslinked pulps, hardwood, softwood, and synthetic fibers. Airlaid and wetlaid structures typically include binding agents, which are used to stabilize the structure. In addition, various foams, absorbent films, and superabsorbent fabrics can be used as an absorbent material. Various acceptable absorbent materials are disclosed in U.S. Pat. No. 5,147,343 for Absorbent Products Containing Hydrogels With Ability To Swell Against Pressure, U.S. Pat. No. 5,601,542 for Absorbent Composite, and U.S. Pat. No. 5,651,862 for Wet Formed Absorbent Composite, all of which are hereby incorporated herein by reference. Furthermore, the proportion of high-absorbency particles can range from about 0 to about 100%, and the proportion of fibrous material from about 0 to about 100%. Additionally, high absorbency fibers can be used such as Oasis type 121 and type 122 superabsorbent fibers available from Technical Absorbent Ltd., Grimsby, Lincolnshire, United Kingdom.

The retention portion preferably can be made of a single or dual layer of absorbent material. In one embodiment, the retention portion has an hour-glass shape with enlarged end regions. Alternatively, the retention portion is substantially rectangular. The retention portion can include a folded or multi-layered configuration. Likewise, the entire absorbent insert can have a folded configuration, with various folds formed from one or more of the backsheet, top sheet, retention portion or other components. The retention portion can have a length substantially equal to, or slightly shorter than, the length of the absorbent insert. The retention portion can include one or more barrier layers attached to the absorbent material. In one embodiment, an upper tissue substrate 74 is disposed adjacent the retention portion. Alternatively, a lower tissue substrate 75 can be disposed adjacent an opposite side of the retention portion, or the tissue can completely envelope the retention position.

Referring to FIGS. 6, 7, 10 and 11, the body side of the opposite end regions of the absorbent insert 50, and in particular, the inner, body side surface of the top sheet 64, are connected to the garment side surface 12 of the first and second body panels 4, 6 at attachment locations 88. In an alternative embodiment, shown FIGS. 8 and 9, the absorbent insert, and in particular the garment side thereof, is connected to the body side surface 10 of the first and second body panels. It should be understood that the absorbent insert 50 can be secured using any of the methods of attachment described above, including for example various adhesives, stitching or other bonding methods. The absorbent insert can be secured to the body panels with any configuration of attachment lines, swirls, patterns, spots, etc., or can be a full and continuous attachment therebetween.

Figure 26:
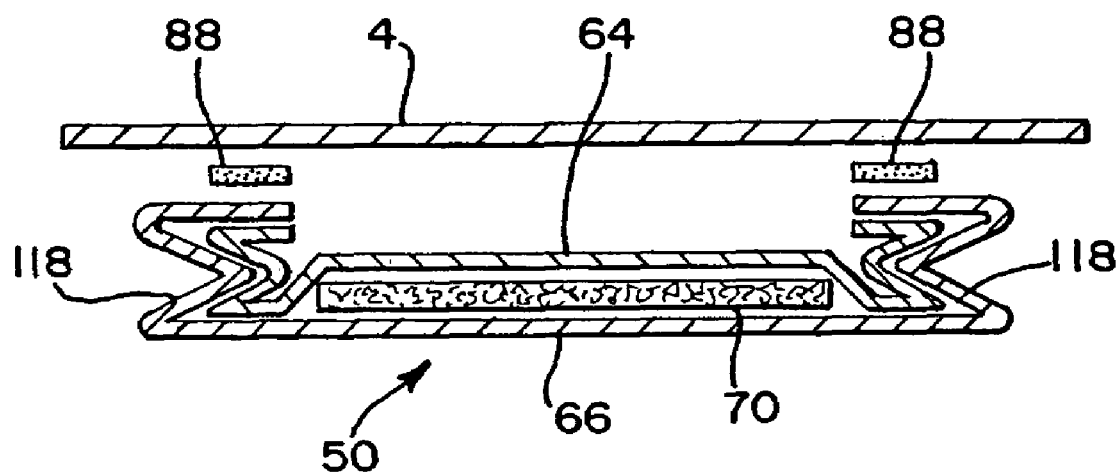
FIG. 26 is a cross-sectional view of an alternative embodiment of a crotch member secured to a body panel.
Figure 27:
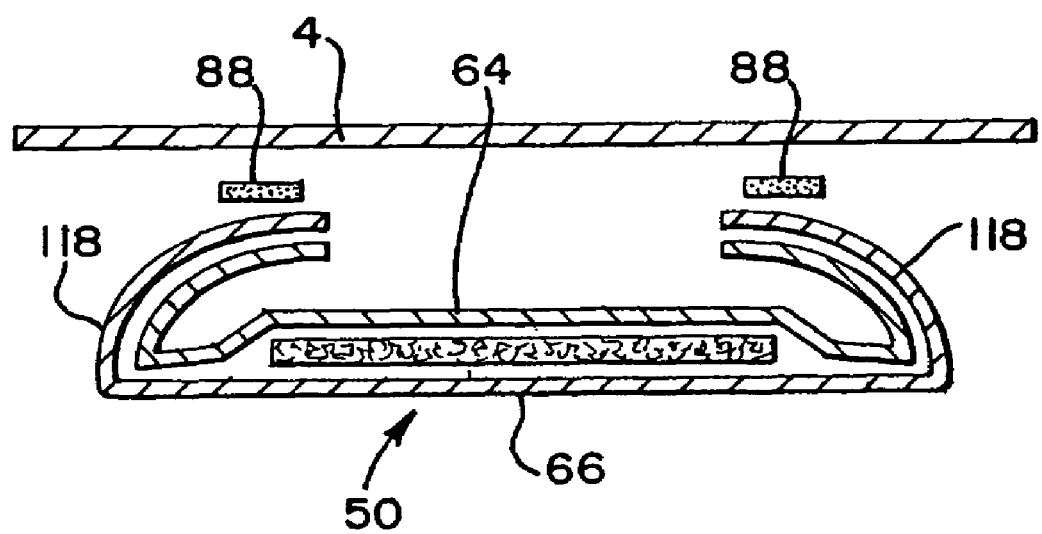
FIG. 27 is a cross-sectional view of an alternative embodiment of a crotch member secured to a body panel.

Referring to FIGS. 26 and 27, the crotch member 50, and in particular one or more of the top sheet 64, back sheet 66, and retention portion 70, are pleated and formed with at least a pair of folds 118, which allow the crotch member 50 to unfold as the body panel material is stretched or elongated. The folds can be Z-shaped (FIG. 26), C-shaped (FIG. 27), or have any other configuration.

In one embodiment, the crotch member 50 is secured to the body panel 4, 6 material after the body panel material is elongated. In this way, the body panel material can be relaxed so as to gather the crotch member.

In another embodiment, the crotch member is minimally attached to the body panel, for example along an attachment line in line with the slit at the centerline of the crotch member. In this way, the crotch member does not inhibit or restrict the ability of the body panel to stretch.

In another embodiment, as one or both of the body panel members 4, 6 are elongated, with the attendant application of a tensile force, the absorbent insert, which includes in one embodiment an extensible top sheet 64 and a stretchable/elastic back sheet 66, stretches or elongates with the body panels.

The back sheet 66 can be elongated in these various embodiments between about 20% and about 150%, between about 40% and about 125% and between about 50% and about 100%. Since, in one embodiment, the retention portion 70 is free floating, or alternatively is minimally attached to the stretchable top sheet and the stretchable/elastic back sheet, e.g., along the longitudinal center line, the retention portion 70 does not restrict the elongation of the back sheet 66 and top sheet 64, or the attached body panels 4, 6.

As shown in FIGS. 6 and 7, an outer cover 102 can be secured to the garment side surface 12 of the front body panel 4 over the end portion 60 of the crotch member 50 so as to improve the aesthetics thereof. In one embodiment, the outer cover has substantially the same shape as the front body panel, and has a length less than the overall length of the undergarment measured between the opposite waist edges thereof. In other embodiments, the outer cover has a lesser area than the front body panel, but is sufficient to cover the end portion of the absorbent insert. In this embodiment, the outer cover can have various shapes including without limitation a rectangular, circular, trapezoidal or square shape. The outer cover 102 is preferably made of a non-woven material, for example, a spun-bond material. In other embodiments, an outer cover is also secured to the garment side surface of the rear body panel over the end portion of the absorbent insert attached thereto. In yet another embodiment, an outer cover extends substantially the length of the undergarment and is secured to the garment side surfaces of both the front and rear body panel.

Referring to FIGS. 8-13, in one embodiment, the crotch edges 16, 24 of the front and rear body panels have a longitudinally extending slit 104 formed therein. In other embodiments, a plurality of spaced apart slits are formed in the crotch edge. The slit 104 is covered by the crotch member 50, which is connected to one of the garment side or body side 10, 12 of the body panels 4, 6. The front and rear body panels each have a length Lf, Lr, while the slit in each has a length Lsf, Lsr. In various embodiments the length of the slits Lsf, Lsr are between about 5% and about 75% of the body panel lengths Lf and Lr respectively. In other embodiments, the length of the slits Lsf, Lsr are between about 10% and about 50% of the body panel lengths Lf and Lr respectively. While in other embodiments, the length of the slits Lsf, Lsr are between about 15% and about 30% of the body panel lengths Lf and Lr respectively. It should be understood that the slits can be formed in only one of the front and rear body panels. In other embodiments, a plurality of longitudinally extending slits are formed in one or both of the front and rear body panel crotch edges. In various embodiments the slit has a length Lsf, Lsr of between about 0.10 inches and 1.50 inches, between about 0.25 inches and about 1.50 inches, between about 0.50 inches and about 1.00 inches, or about 0.75 inches.

Referring to FIG. 6, the crotch edge 16, 24 of each of the front and rear body panels has a cut-out 106 formed therein. The cut-out 106 extends generally inward from a plane defined by the innermost crotch portion, and in one embodiment has a generally concave shape. The cut-out can be circular, semi-circular, oval shaped, half oval-shaped, rectangular, triangular, diamond, hexagonal, pentagonal, trapezoidal or any other shape. In this way, the cut-out 106 provides access to the crotch member 50 lying therebeneath (when attached to the garment side surface of the body panel), or provides room for the crotch member 50 to expand outwardly away from the body of the user (when attached to the body side surface of the body panel). The slits 104 formed in the body panels shown in FIGS. 8-11 perform the same function. It should be understood that the cut-out 106 may be formed in only one of the front and rear body panels. In other embodiments, one of the body panels has a slit, while the other has a cutout. In yet another embodiment, the body panel has a cutout, with a slit extending from the edge of the cutout. In yet another embodiment, the material removed to form the cut-out is not completely separated from the body panel(s), but rather is folded over the body panel to provide reinforcement, for example at the region where the crotch member is attached.

In operation, the user applies the undergarment to their body, whether by way of pulling it up around their waist as a pant-like garment or by way of fastening it about their waist with fasteners as a diaper-like garment. As the garment is applied or fitted to the body of the user, the front and rear body panels 4, 6 are elongated from a first condition, preferably relaxed, to a second condition, preferably elongated, in at least one direction, preferably the lateral direction 502. Of course, the body panel members can also elongate in the longitudinal direction 500 from the crotch to the waist. In one embodiment, one or both of the body panels 4, 6 is elongated in a lateral direction 502 between about 20% and about 300%, in another embodiment between about 50% and about 200%, and in another embodiment between about 100% and about 150%, as it is applied to the user. The body panel members are elongated by virtue of a tensile force being applied thereto as they conform to the body of the user.

Figure 12:
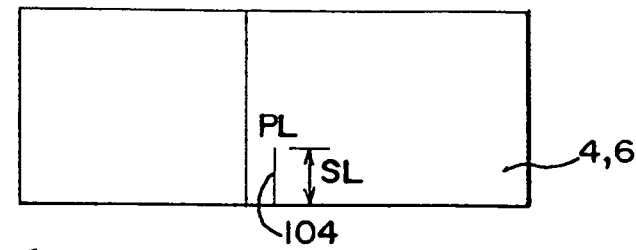
FIG. 12 is a plan view of a portion of body panel web in an unstretched condition with a slit formed therein.
Figure 13:
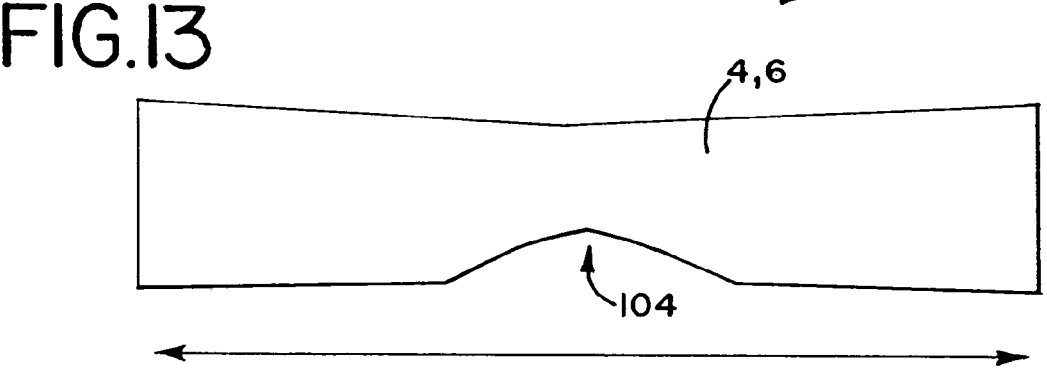
FIG. 13 is a plan view of the portion of body panel web shown in FIG. 12 in a stretched condition.
Figure 14:
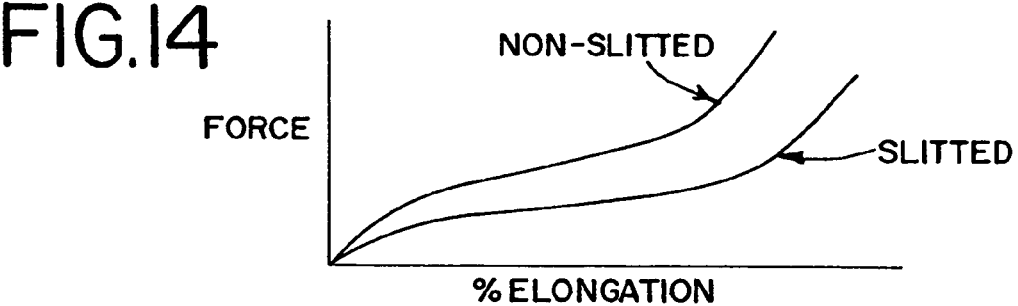
FIG. 14 is a schematic graphical representation of the force required to elongate a body panel v. the percent elongation thereof for various body panel configurations.

Referring to FIGS. 12-14, when a body panel 4, 6 having a slit 104 formed therein is elongated in a direction substantially perpendicular to the slit, the body panel can be more easily elongated. In essence, the force required to elongate the body panel is reduced. In this way, the undergarment can be made to more easily conform to the body of the user and does not provide an overly restrictive feel to the user. It should be understood that the cut-out can serve the same function.

Referring to FIGS. 15-25, a body panel material was tested to determine the effect of a slit on the force required to elongate the material. In particular, a VFL body panel material was tested. The material is a three-ply laminate having inner and outer facing layers of 0.46 ounces per square yard (osy) polypropylene spunbond material (Kimberly-Clark Delta white polypropylene spunbond) and a middle layer of 10 grams per square meter (gsm) Kraton® 666 elastomer strands (3 mm apart) elongated to 4.5 to 5.5 times. The three piece laminate is adhesively laminated with 2.5 gsm Bostik Findley H2096 adhesive.

Figure 15:
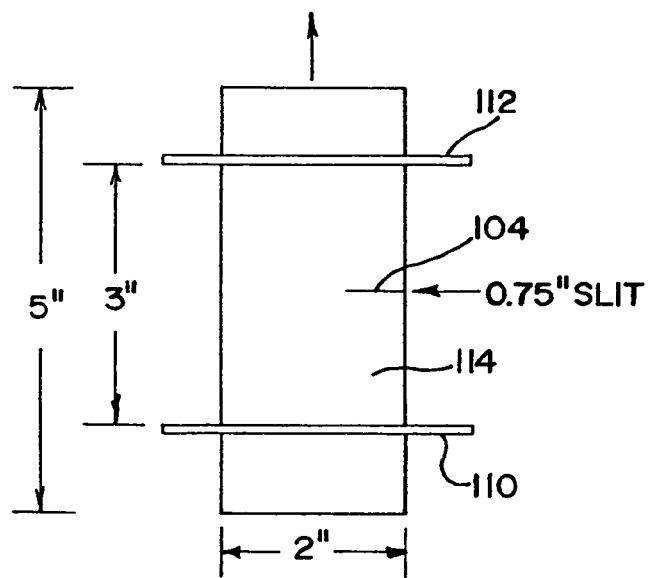
FIG. 15 is a schematic representation of a test sample and procedure for comparing load v. % strain relationships.
Figure 16:
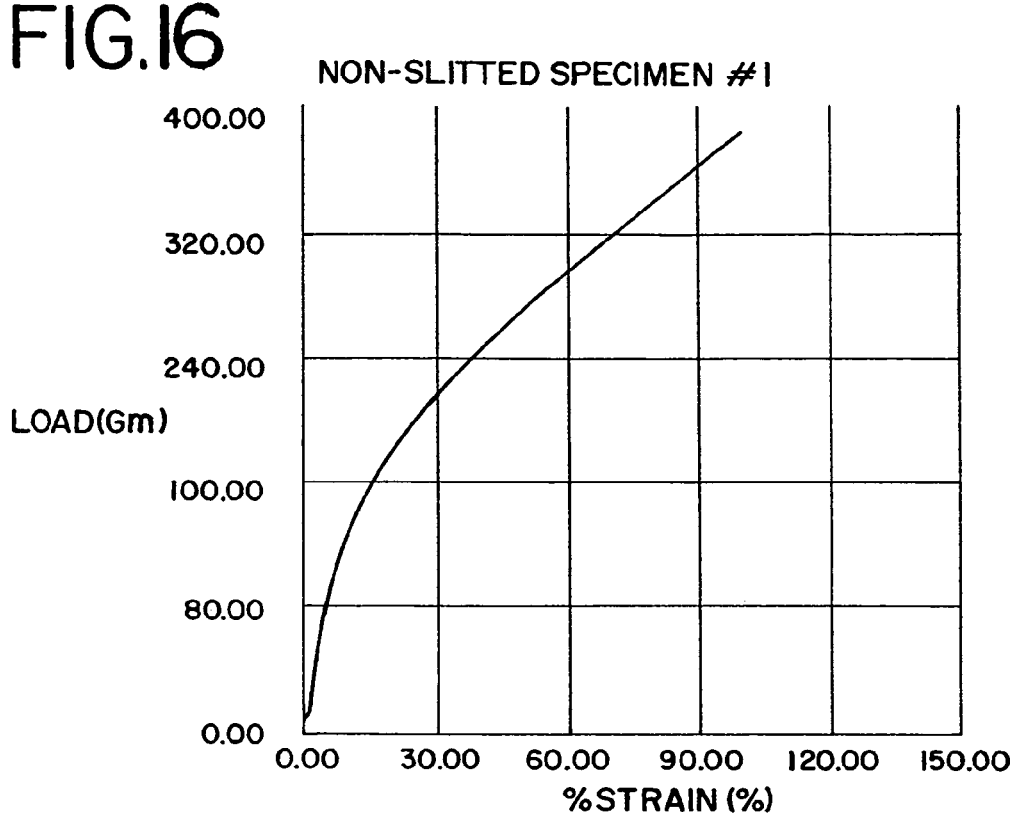
FIG. 16 is a load v. % strain graph for a first test specimen without a slit.
Figure 17:
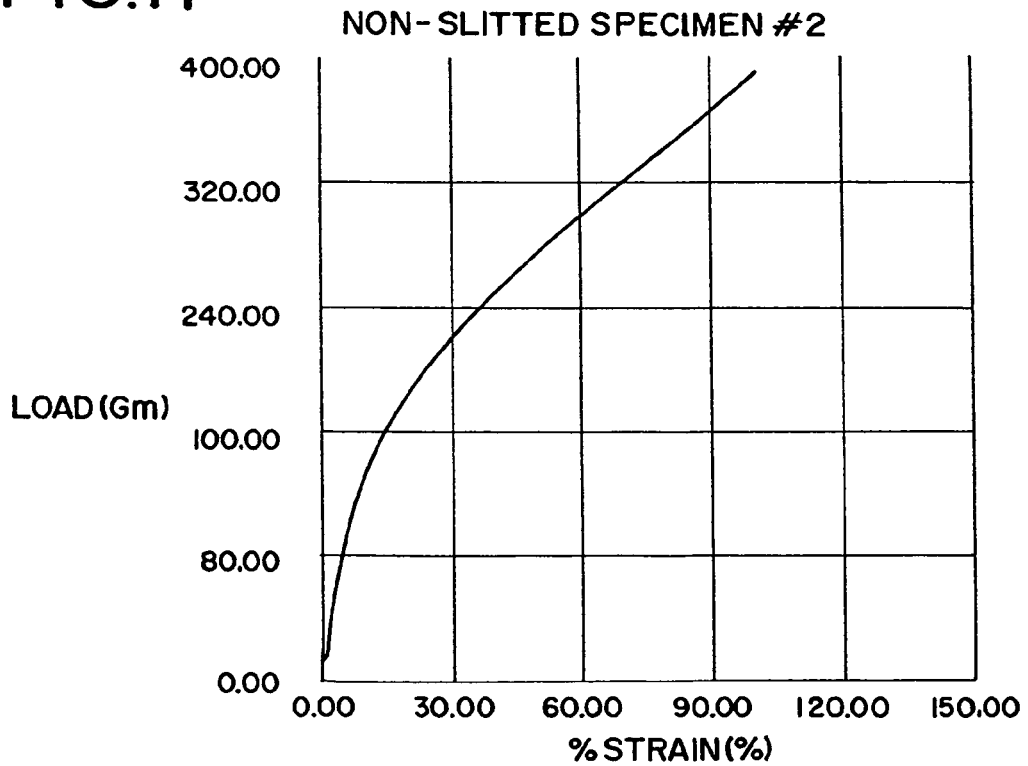
FIG. 17 is a load v. % strain graph for a second test specimen without a slit.
Figure 18:
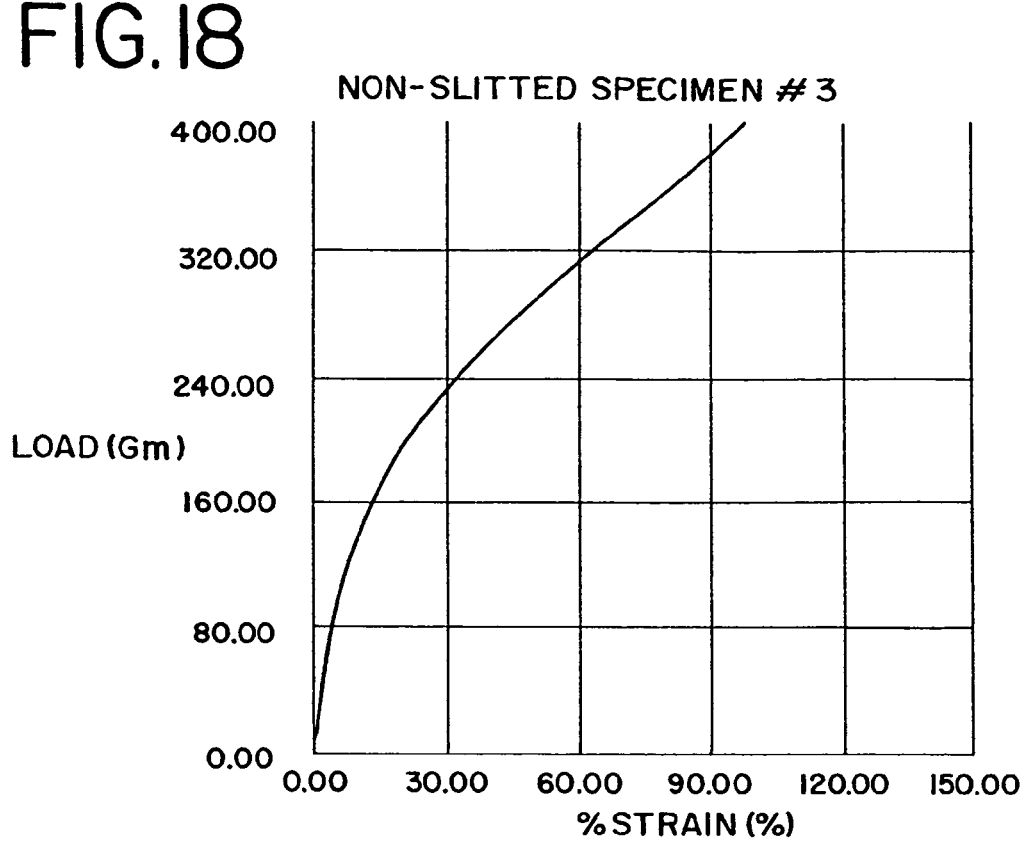
FIG. 18 is a load v. % strain graph for a third test specimen without a slit.
Figure 19:
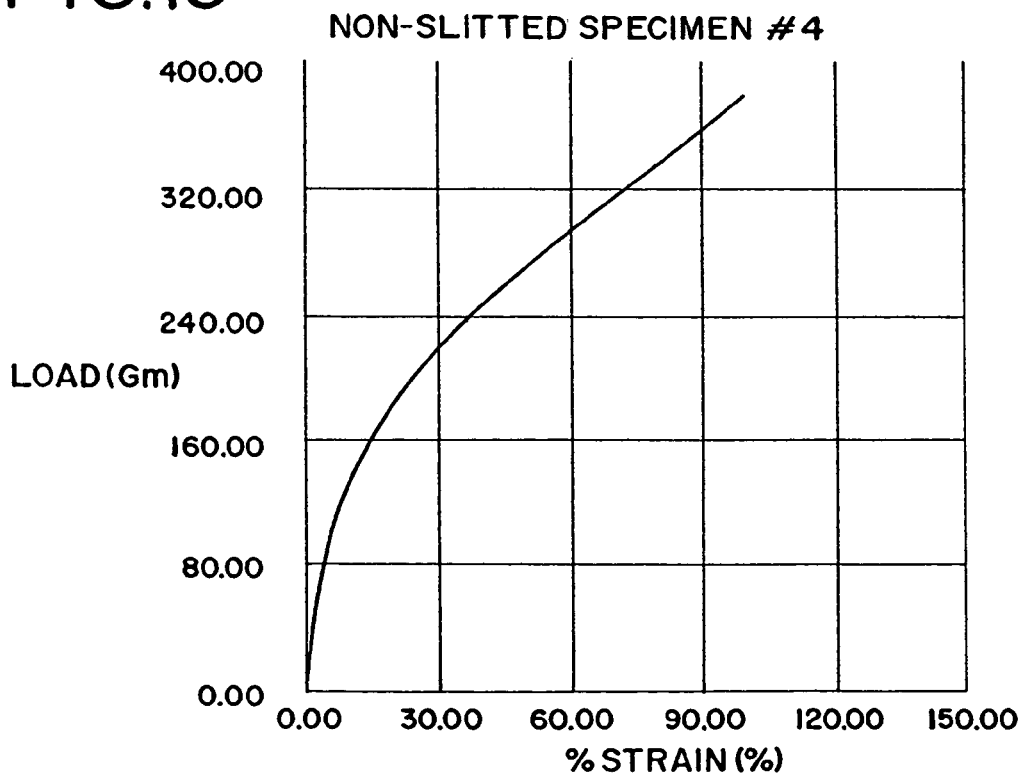
FIG. 19 is a load v. % strain graph for a fourth test specimen without a slit.
Figure 20:
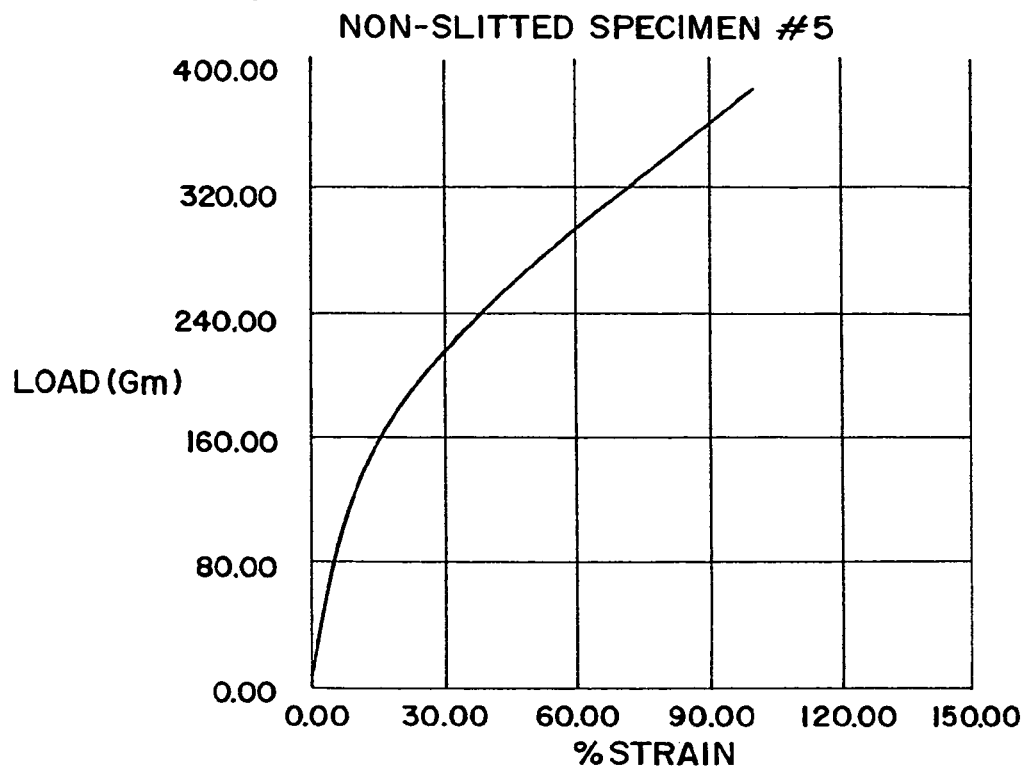
FIG. 20 is a load v. % strain graph for a fifth test specimen without a slit.
Figure 21:
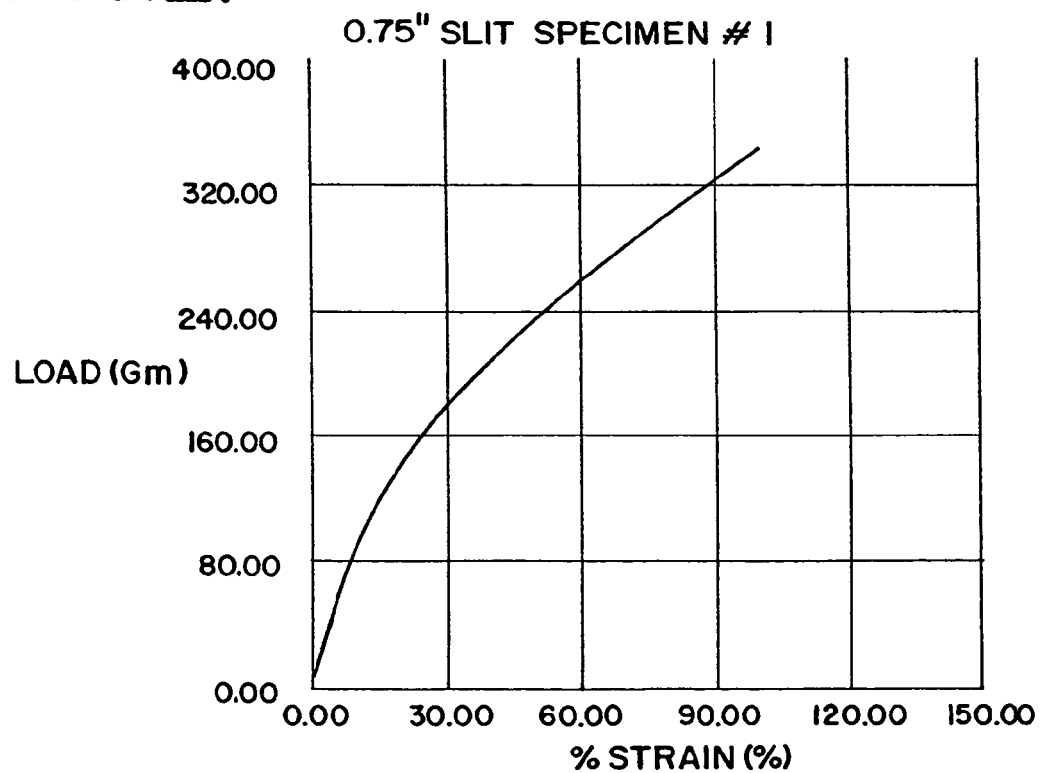
FIG. 21 is a load v. % strain graph for a first test specimen with a slit.
Figure 22:
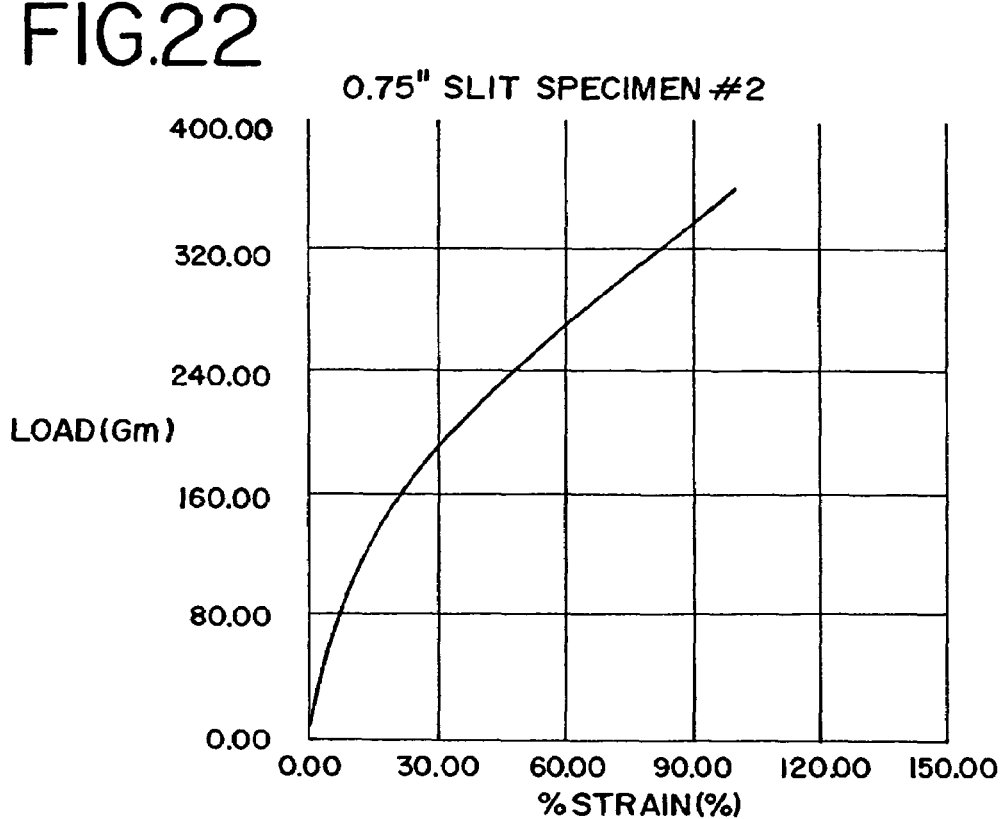
FIG. 22 is a load v. % strain graph for a second test specimen with a slit.
Figure 23:
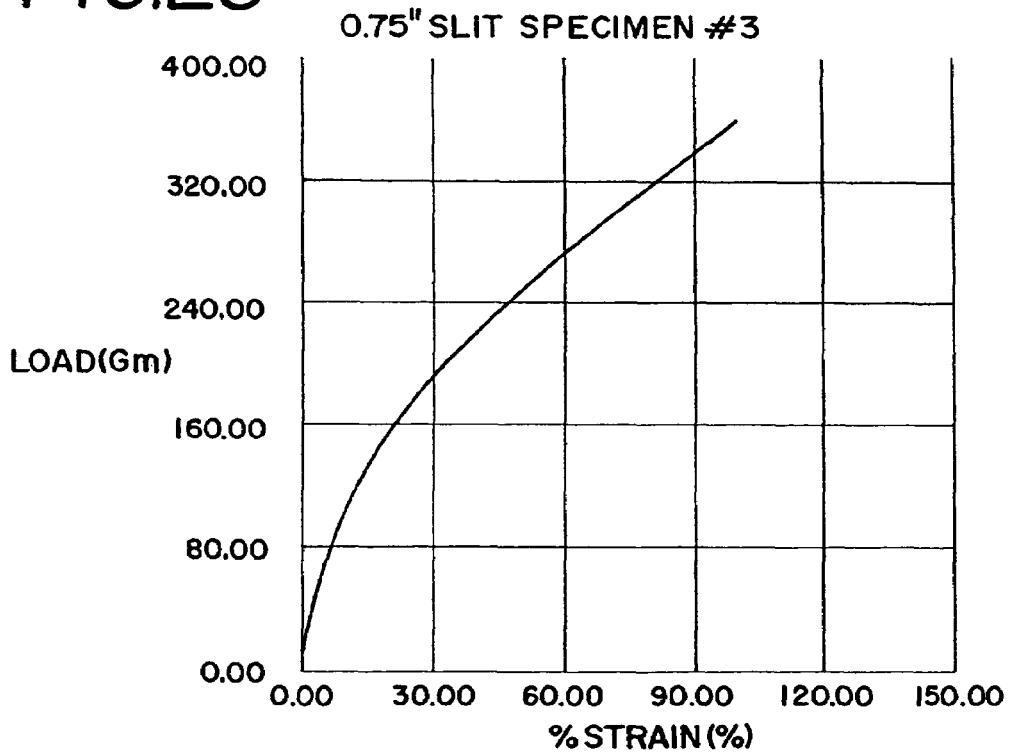
FIG. 23 is a load v. % strain graph for a third test specimen with a slit.
Figure 24:
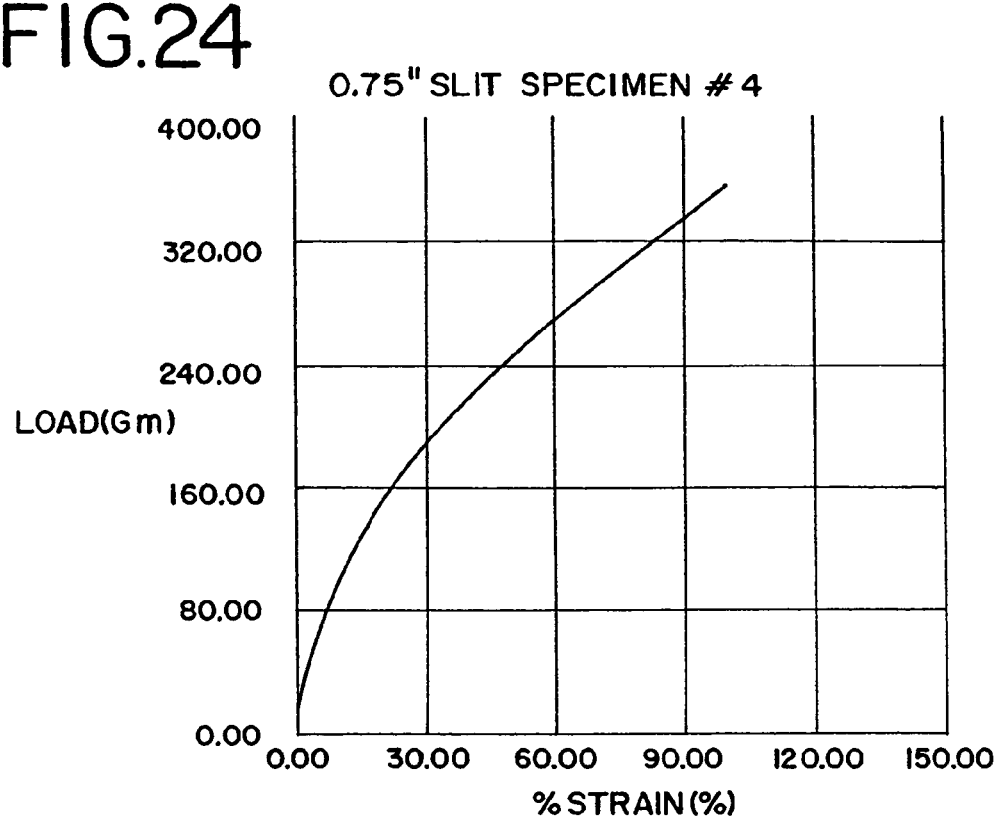
FIG. 24 is a load v. % strain graph for a fourth test specimen with a slit.
Figure 25:
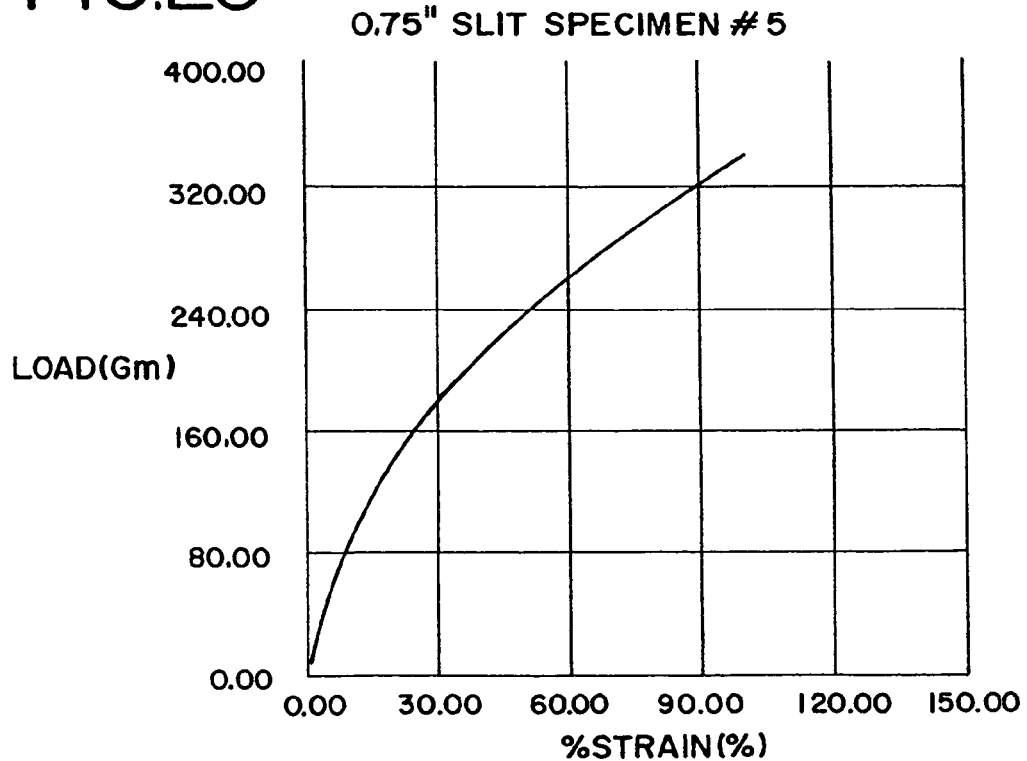
FIG. 25 is a load v. % strain graph for a fifth test specimen with a slit.

The test procedure for testing the body panel material is as follows:

I. Sample Preparation:
  1. Ten specimens 114 of 2 inches wide by 5 inches long were cut from a sheet of VFL material. The stretchable direction of the material is the length direction of the specimens, which is also the test direction.
  2. A slit 104 of 0.75 inches was cut in five of the specimens, as shown in FIG. 15.

II. Tensile Test:
  1. The tensile test was conducted on a tensile tester (Model: Synergie 200 available from MTS located at 14000 Technology Drive, Eden Prairie, Minn.) located in an environmental room where the temperature was kept at 23 degree C. and the relative humidity was kept at 50%.
  2. The initial distance between the lower (stationary) and the upper (moving) jaws 110, 112 of the tensile tester was set at 3 inches, as shown FIG. 15.
  3. The specimen was clamped onto the jaws, with the slit located half way between the two jaws.
  4. The moving (upper) jaw was activated to travel at a constant speed of 10 inches/min away the stationary (lower) jaw. The moving jaw was stopped at an extension of 3 inches (100% extension). The load limit was 10 kg.
  5. The load (grams) v. % strain curve was recorded on a computer equipped with TestWorks Version 3.10 software program available from MTS.
  6. The load (grams) at 100% strain and the total energy (gram-cm) applied to the specimen during the stretching were also recorded.
  7. Five specimens without a slit and five specimens with a slit were tested.

The load v. % strain curves for the ten specimens are shown in FIGS. 16-25. In addition, the Load at 100% Strain (gm) and Total Energy (gm-cm) for each sample are shown in Tables 1 and 2.

TABLE 1

Unslit Specimens

|  | Load at 100% Strain Gm | Total Energy Gm-cm |
|---|---|---|
| 1 | 382.9 | 1955.89 |
| 2 | 389.3 | 1978.08 |
| 3 | 402.8 | 2078.56 |
| 4 | 378.5 | 1944.97 |
| 5 | 380.4 | 1950.50 |
| Mean | 386.8 | 1981.60 |
| Min | 378.5 | 1944.97 |
| Max | 402.8 | 2078.56 |
| StdV | 9.8 | 55.64 |
| % Cov | 2.5 | 2.81 |

TABLE 2

Slit Specimens

|  | Load at 100% Strain Gm | Total Energy Gm-cm |
|---|---|---|
| 1 | 344.0 | 1680.55 |
| 2 | 358.8 | 1760.50 |
| 3 | 359.7 | 1782.71 |
| 4 | 356.5 | 1765.68 |
| 5 | 339.3 | 1664.52 |
| Mean | 351.6 | 1730.79 |

TABLE 2-continued

Slit Specimens

|  | Load at 100% Strain Gm | Total Energy Gm-cm |
| --- | --- | --- |
| Min | 339.3 | 1664.52 |
| Max | 359.7 | 1782.71 |
| StdV | 9.4 | 54.11 |
| % Cov | 2.7 | 3.13 |

When looking at the data shown in FIGS. 16-25 and Tables 1 and 2, it is readily apparent that the loads for the slit specimens are lower than the loads for the non-slit specimens at any given strain. This finding indicates that it is easier to stretch an elastic panel with a slit.

In addition, the average load at 100% strain for the non-slit specimens is about 387 grams while the average load at 100% strain for the slit specimens (0.75 inch slit) is about 352 grams. This represents about a 10% difference in the force required to stretch a slit and a non-slit specimen.

Moreover, the average total energy required to stretch the non-slit specimens to 100% is about 1982 grams-cm while the average total energy requires to stretch the slit specimens to 100% is about 1731 grams-cm. This represents about 14% difference in the energy required to stretch a slit and a non-slit specimen.

In another aspect, the manufacturer or retailer of the aforedescribed absorbent garments provides instructional information to the user, for example by way of textual or pictorial indicia on the packaging materials, about how the garment works. For example, the manufacturer or retailer can explain to the end user the advantages of the stretchable/elastic absorbent insert, the slit and/or the cutout, and the resultant ability of the body panels to freely conform to the body of the user without restriction from the retention portion, thereby improving the conformance and fit of the garment.

Referring to FIGS. 1-3, the method for fabricating one or more embodiments of the aforedescribed undergarments is illustrated. In particular, a web 72 of body panel material is cut in a longitudinal machine direction 74 to form a front and rear body panel web 76, 78 each having a cut edge 80, 82 and an outer lateral edge 84, 86. In one embodiment, as shown in FIGS. 1 and 2, the cut edges 80, 82 are linear. In another embodiment, shown in FIG. 3, the cut edges 80, 82 have a non-linear profile, and can be formed for example as undulating wave pattern. In one embodiment, the web is cut in a sinusoidal wave pattern, which should be broadly interpreted as a pattern having peaks and valleys. The pattern can be formed of undulating curves or wave patterns, or can include or be made entirely of various linear portions. In this way, the front body panel can be provided with a different shape than the rear body panel.

Referring to the embodiments of FIGS. 1 and 2, a die cutter is used to successively make a plurality of cutouts 90 spaced apart in the machine direction. The cutouts 90 can have a multitude of shapes, as explained above, including the circular shaped shown in FIG. 2, the oval, or egg shape shown in FIG. 1, or the semi-circular, half oval-shaped, rectangular, triangular, diamond, hexagonal, pentagonal, trapezoidal or any other shape as explained above. After the cutout 90 is made, the web is cut along the machine direction to form the cut edges 80, 82 as just explained. The cut can be made such that the cut edges 80, 82 intersect the cutout 90, as shown in FIG. 1, such that each of the front and rear body panel webs 76, 78 has a cutout 92, or it can be offset on one side of the cutout 90 such that only one of the body panel webs has a cutout 90 as shown in FIG. 2. In such an embodiment, the front and rear body panels can be provided with different strain and elongation properties.

Referring to FIG. 3, the cut edges 80, 82 and cutout can be formed simultaneously, for example with a die cutter.

Alternatively, as shown in FIG. 4, the web is first cut to form a front and rear body panel web 76, 78, or two webs are fed independently in the machine direction 94, and a cutout 92 is formed in each web independently, albeit in one embodiment by a single cutter device.

In all of the embodiments of FIGS. 1-4, the front and rear body panel webs 76, 78 are also separated, or shifted, outwardly relative to one another in the lateral cross-direction 94 so as to form a gap 96 between the cut edges 80, 82 of the front and rear body panel webs 76, 78. If, in FIG. 4, the webs 76, 78 are fed independently into the machine in a spaced apart relationship, then no shifting is required. Referring to FIGS. 1-4, the crotch member 50 is applied over the cutouts 90, 92 and is secured to one of the body side or garment side surfaces of the body panel webs 76, 78. The webs 76, 78 can be thereafter cut in the cross-machine direction, as is well know in the art, to form the individual undergarments.

Referring to FIG. 5, a cutout is formed in a body panel web 72, which is not slit or otherwise cut in the machine direction and generally extends from one waist edge of the garment to the other. A crotch member 50 is applied over and covers the cutout 98 as it is secured to one of the bodyside or garment side surfaces of the body panel web 72. When attached to the body side surface of the body panel, the crotch member, which is configured in one embodiment as an absorbent insert, expands through the cutout 98 or opening as it is insulted during use.

In various embodiments, the spacing between the cut edges 80, 82 of the respective front and rear body panels is between about 10 mm and about 800 mm, between about 50 mm and about 500 mm, or between about 100 mm and about 300 mm. In an alternative embodiment, the cut edges 80, 82 and the crotch portions of the front and rear body panels overlap, and can be secured one to the other. In such an embodiment, the panels can be separated slightly, or can simply be shifted in the longitudinal direction without any lateral separation.

Cross-machine direction slits 104 formed in the front and rear body panels can be formed in the same way as the cut-outs 90, 92 described above. In particular, the slits 104 can be first formed in a web, which is thereafter cut in the longitudinal machine direction through the slits to form front and rear body panel webs each having a slit extending transversely to the cut edges. Alternatively, the web can first be cut in the machine direction, with the slits thereafter formed in the cross-machine direction, before or after the front and rear body panel webs are separated. In yet another alternative, the slits and cut edges are formed simultaneously.

The cutouts 90, 92 and slits 104 can be formed in the body panel webs, which are elastic, while they are in either a stretched or relaxed condition. Likewise, the crotch members 50 can be secured to the body panel webs 72, 76, 78 while the body panel webs are in a stretched or relaxed condition. The edges formed by the slit are substantially abutted when the body panel webs are in the relaxed condition, while they are separated when the body panel webs are in the stretched condition. The slits and cutouts can be made through the leg elastic elements, which may be disposed along the entirety of the cut edges on both the front and rear body panel webs. If the leg elastics are in tension, this may tend to open the slit or cutout after the leg elastics are severed. The leg elastics can be deadened or otherwise omitted or removed to avoid such separation.

It should be understood that the body panel webs can be cut to form the cut edges, separated in the cross-direction, and also shifted in the longitudinal direction, as disclosed for example and without limitation in U.S. patent application Ser. No. 10/261,805, filed Oct. 1, 2002 and entitled "Three-Piece Disposable Undergarment and Method in the Manufacturing Thereof," which is hereby incorporated herein by reference. The slits or cutouts in the body panel web that is shifted forwardly relative to the other body panel web, are aligned with the next positioned slit or cutout in the other body panel web, such that each undergarment has a slit or cutout formed in each of the front and rear body panel webs. Of course, it should be understood that only of the front and rear body panel webs may be provided with a cutout or slit.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. A method of manufacturing a disposable undergarment comprising:
    moving a web of body panel material in a longitudinal machine direction, said web of body panel material having first and second spaced apart outer edges;
    forming a cutout in said web and thereby removing a portion of said body panel material from said web;
    cutting said web of body panel material along said longitudinal machine direction and thereby forming a rear body panel web and a front body panel web, wherein said cutting said web of body panel material comprises forming first and second cut edges on said front and rear body panel webs, wherein said removed portion of said body panel material does not form any part of said front and rear body panel webs, and wherein said cutout extends from at least one of said first and second cut edges toward a respective one of said first and second outer edges; and
    connecting a crotch member to each of said rear and front body panel webs, wherein said crotch member covers an entirety of said cutout, wherein said crotch member comprises an elastic material.

2. The method of claim 1 wherein said cutting said web comprises cutting said web such that said cutout is formed entirely in one of said front and rear body panel webs.

3. The method of claim 1 wherein said cutting said web comprises cutting said web such that a portion of said cutout is formed in each of said front and rear body panel webs.

4. The method of claim 1 wherein said cutout has a substantially circular shape.

5. The method of claim 1 wherein said first and second cut edges are non-linear.

6. The method of claim 1 wherein said first and second cut edges are substantially linear.

7. The method of claim 1 wherein said web has a body side surface and a garment side surface, and wherein said connecting said crotch member to each of said front and rear body panel webs comprises connecting said crotch member to said garment side surface of each of said front and rear body panel webs.

8. The method of claim 1 wherein said web has a body side surface and a garment side surface, and wherein said connecting said crotch member to each of said front and rear body panel webs comprises connecting said crotch member to said body side surface of each of said front and rear body panel webs.

9. The method of claim 1 further comprising
    stretching said web in said longitudinal machine direction to a stretched condition prior to said forming said cutout in said web and forming said cutout in said web while said web is in said stretched condition.

10. The method of claim 1 wherein said forming said cutout and cutting said web of body panel material along said longitudinal machine direction are done simultaneously with a single cutting device.

11. The method of claim 1 further comprising separating said front and rear body panel webs prior to connecting said crotch member thereto.

12. The method of claim 1 wherein said crotch member comprises a top sheet, a back sheet and a retention portion disposed between said top sheet and said back sheet.

13. The method of claim 1 wherein said crotch member comprises at least one fold, wherein said connecting said crotch member to said front and rear body panel webs comprises connecting said at least one fold to said front and rear body panel webs.

14. The method of claim 1 wherein said cutting said web of body panel material is performed separately from and before said forming said cutout in said web.

15. A method of manufacturing a disposable undergarment comprising:
    moving a web of body panel material in a longitudinal machine direction, said web of body panel material having first and second spaced apart outer edges;
    forming a cutout in said web and thereby removing a portion of said body panel material from said web, wherein said cutout has a substantially oval shape;
    cutting said web of body panel material along said longitudinal machine direction and thereby forming a rear body panel web and a front body panel web, wherein said cutting said web of body panel material comprises forming first and second cut edges on said front and rear body panel webs, wherein said removed portion of said body panel material does not form any part of said front and rear body panel webs, and wherein said cutout extends from at least one of said first and second cut edges toward a respective one of said first and second outer edges; and
    connecting a crotch member to each of said rear and front body panel webs, wherein said crotch member covers an entirety of said cutout.

16. A method of manufacturing a disposable undergarment comprising:
    moving a web of body panel material in a longitudinal machine direction, said web of body panel material having first and second spaced apart outer edges;
    forming a cutout in said web and thereby removing a portion of said body panel material from said web;
    cutting said web of body panel material along said longitudinal machine direction and thereby forming a rear body panel web and a front body panel web, wherein said cutting said web of body panel material comprises forming first and second cut edges on said front and rear body panel webs, wherein said removed portion of said body panel material does not form any part of said front and rear body panel webs, and wherein said cutout extends from at least one of said first and second cut edges toward a respective one of said first and second outer edges;

connecting a crotch member to each of said rear and front body panel webs, wherein said crotch member covers an entirety of said cutout; and stretching at least one of said front and rear body panel webs to a stretched condition prior to said connecting said crotch member thereto and connecting said crotch member to said at least one of said front and rear body panel webs when in said stretched condition.

17. A method of manufacturing a disposable undergarment comprising:

moving a web of body panel material in a longitudinal machine direction, said web of body panel material having first and second spaced apart outer edges;

forming a cutout in said web and thereby removing a portion of said body panel material from said web;

cutting said web of body panel material along said longitudinal machine direction and thereby forming a rear body panel web and a front body panel web, wherein said cutting said web of body panel material comprises forming first and second cut edges on said front and rear body panel webs, wherein said removed portion of said body panel material does not form any part of said front and rear body panel webs, and wherein said cutout extends from at least one of said first and second cut edges toward a respective one of said first and second outer edges, and wherein said cutting said web of body panel material is performed separately from and after said forming said cutout in said web; and connecting a crotch member to each of said rear and front body panel webs, wherein said crotch member covers an entirety of said cutout.

* * * * *

UNITED STATES PATENT AND TRADEMARK OFFICE
CERTIFICATE OF CORRECTION

PATENT NO. : 7,635,360 B2  Page 1 of 1
APPLICATION NO. : 10/624660
DATED : December 22, 2009
INVENTOR(S) : Van Gompel et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 995 days.

Signed and Sealed this

Ninth Day of November, 2010

David J. Kappos
*Director of the United States Patent and Trademark Office*